United States Patent [19]

Finkelstein et al.

[11] Patent Number: 5,234,917

[45] Date of Patent: Aug. 10, 1993

[54] SUBSTITUTED 5-(ALKYL)CARBOXAMIDE IMIDAZOLES

[76] Inventors: Joseph A. Finkelstein; Judith Hempel; Richard M. Keenan; James Samanen; Joseph Weinstock, all of SmithKline Beecham Corp., Corporate Patents N-160, P.O. Box 7929, Philadelphia, Pa. 19101

[21] Appl. No.: 621,491

[22] Filed: Nov. 30, 1990

Related U.S. Application Data

[63] Continuation-in-part of Ser. No. 459,051, Dec. 29, 1989, abandoned.

[51] Int. Cl.$^5$ ............... A61K 31/675; C07D 233/54; C07D 277/04; C07D 277/30; C07D 249/04; C07D 263/34; C07D 261/04; C07F 9/06
[52] U.S. Cl. .................... 514/397; 548/312.7; 548/111; 548/112; 548/119; 548/334.5; 548/337.1; 548/312.4; 548/333.5; 548/338.1; 548/251; 548/253; 548/314.7; 548/187; 548/194; 548/204; 548/225; 548/315.1; 548/264.4; 548/265.4; 548/266.6; 548/225; 548/315.7; 548/233; 548/236; 548/243; 548/245; 548/315.4; 548/247; 548/321.5; 548/324.1; 548/323.1; 548/331.5; 548/328.1; 548/328.5; 548/332.1; 548/333.1; 546/22; 546/24; 546/278; 514/398; 514/399; 514/400; 514/381; 514/382; 514/369; 514/370; 514/365; 514/341; 514/383; 514/384; 514/359; 514/374; 514/376; 514/377; 514/378; 514/380; 514/90; 514/93; 514/94; 514/89
[58] Field of Search ............... 548/342, 111, 112, 119, 548/336, 337, 339, 343, 251, 253, 187, 194, 204, 255, 264.4, 265.4, 266.6, 225, 233, 236, 243, 245, 247; 514/397, 398, 399, 400, 381, 382, 397, 369, 370, 365, 341, 383, 384, 359, 374, 376, 377, 378, 380, 89, 90, 93, 94

[56] References Cited

U.S. PATENT DOCUMENTS

| 4,340,598 | 7/1982 | Furukawa et al. | 548/342 |
| 4,355,040 | 10/1982 | Furukawa et al. | 548/342 |

FOREIGN PATENT DOCUMENTS

| 0103647 | 3/1984 | European Pat. Off. | 548/342 |
| 0245637 | 11/1987 | European Pat. Off. | 548/342 |
| 0253310 | 1/1988 | European Pat. Off. | 548/342 |
| 0324377 | 7/1989 | European Pat. Off. | 548/342 |
| 1341375 | 12/1973 | United Kingdom | 548/342 |

OTHER PUBLICATIONS

Bolis et al.; J. Med. Chem.; 30; pp. 1729-1737; (1987).
Haber et al.; J. Cardiovas. Pharmacol. (1987) pp. 554-558.
Plattner et al.; J. Med. Chem.; 31; pp. 2277-2288, (1988).
Burger; Medicinal Chemistry 2nd Ed.; (1960) pp. 565-571, 579-601.
Denkewalter et al.; Progress in Drug Research; vol. 10; pp. 510-512 (1966).

Primary Examiner—Mary C. Lee
Assistant Examiner—Robert C. Whittenbaugh
Attorney, Agent, or Firm—Mary E. McCarthy; Stephen Venetianer; Edward T. Lentz

[57] ABSTRACT

Angiotensin II receptor antagonists having the formula:

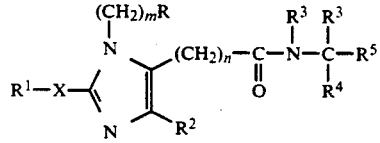

which are useful in regulating hypertension and in the treatment of congestive heart failure, renal failure, and glaucoma pharmaceutical compositions including these antagonists, and methods of using these compounds to produce angiotensin II receptor antagonism in mammals.

20 Claims, No Drawings

SUBSTITUTED 5-(ALKYL)CARBOXAMIDE IMIDAZOLES

This application is a continuation-in-part of U.S. Ser. No. 07/459,015, filed Dec. 29, 1989 now abandoned.

The present invention relates to new substituted 5-(alkyl)carboxamide imidazole compounds which are angiotensin II receptor antagonists and are useful in regulating hypertension induced or exacerbated by angiotensin II and in the treatment of congestive heart failure, renal failure, and glaucoma. This invention also relates to pharmaceutical compositions containing substituted 5-(alkyl)carboxamide imidazoles and methods for using these compounds as antagonists of angiotensin II, as antihypertensive agents and and as agents for treating congestive heart failure, renal failure, and glaucoma.

BACKGROUND OF THE INVENTION

The class of peptide pressor hormone known as angiotensin is responsible for a vasopressor action that is implicated in the etiology of hypertension in man. Inappropriate activity of the renin angiotensin systems appears to be a key element in essential hypertension, congestive heart failure and in some forms of renal disease. In addition to a direct action on arteries and arterioles, angiotensin II (AII), being one of the most potent endogenous vasoconstrictors known, stimulates the release of aldosterone from the adrenal cortex. Therefore, the renin angiotensin system, by virtue of its participation in the control of renal sodium handling, plays an important role in cardiovascular homostasis.

Interruption of the renin angiotensin system with converting enzyme inhibitors, such as captopril, has proved to be clinically useful in the treatment of hypertension and congestive heart failure (Abrams, W. B., et al., (1984), *Federation Proc.*, 43, 1314). The most direct approach towards inhibition of the renin-angiotensin system would block the action of AII at the receptor. Compelling evidence suggests that AII also contributes to renal vasoconstriction and sodium retention that is characteristic of a number of disorders such as heart failure, cirrhosis and complications of pregnancy (Hollenberg, N. K., (1984), *J. Cardiovas. Pharmacol.*, 6, S176). In addition, recent animal studies suggest that inhibition of the renin angiotensin system may be beneficial in halting or slowing the progression of chronic renal failure (Anderson, S., et al., (1985), *J. Clin. Invest.*, 76, 612). Also, a recent patent application (South African Patent Application Number 87/01,653) claims that AII antagonists are useful as agents for reducing and controlling elevated intraocular pressure, especially glaucoma, in mammals.

The compounds of this invention inhibit, block and antagonize the action of the hormone AII, and are therefore useful in regulating and moderating angiotensin induced hypertension, congestive heart failure, renal failure, glaucoma, and other disorders attributed to the actions of AII. When compounds of this invention are administered to mammals, the elevated blood pressure due to AII is reduced and other manifestations based on AII intercession are minimized and controlled. Compounds of this invention are also expected to exhibit diuretic activity.

Recognition of the importance of blocking and inhibiting the actions of AII has stimulated other efforts to synthesize antagonists of AII. The following references have disclosed imidazole derivatives which are described as having AII blocking activity and useful as hypotensive agents.

U.S. Pat. No. 4,340,598 discloses substituted imidazol-5 yl alkanoic acids, and amido and lower alkyl ester derivatives thereof, of the formula:

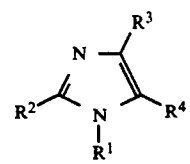

wherein $R^1$ is lower alkyl or phenyl$C_{1-2}$alkyl optionally substituted with halogen or nitro; $R^2$ is lower alkyl, cycloalkyl, or phenyl optionally substituted; one of $R^3$ and $R^4$ is —$(CH_2)_nCOR^5$, where $R^5$ is amino, lower alkoxy or hydroxy and n is 0–2, and the other of $R^3$ and $R^4$ is hydrogen or halogen. Examples include 1-benzyl-2-n-butyl-chloroimidazole-5-acetamide and 1-benzyl-2-n butyl-5-chloroimidazole-4-acetic acid.

U.S. Pat. No. 4,355,040 discloses substituted 1-benzylimidazol-5-yl acetic acid derivatives having the formula:

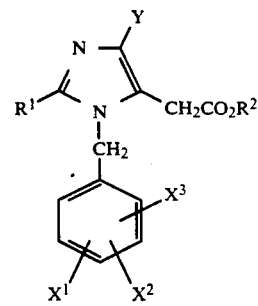

wherein $R^1$ is lower alkyl, cycloalkyl, or phenyl optionally substituted; $X^1$, $X^2$ and $X^3$ are each hydrogen, halogen, nitro, amino, lower alkyl, lower alkoxy, benzyloxy, or hydroxy; Y is halogen and $R^2$ is hydrogen or lower alkyl. A compound specifically disclosed is 1-(2-chlorobenzyl)-2-n-butyl-4-chloroimidazole-5-acetic acid.

European Patent Application 103,647 discloses substituted 1-benzyl-2-phenyl-4-chloroimidazol-5-yl acetic acid derivatives of the formula:

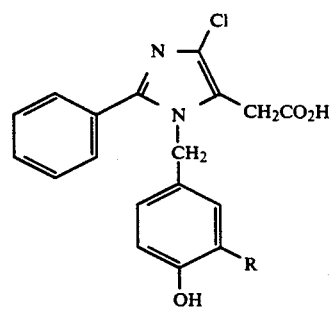

wherein R is lower alkyl. Specifically, the disclosure includes 4-chloro-1-(4-methoxy-3-methylbenzyl)-2-phenyl-imidazole-5-acetic acid.

European Patent Application 245,637 discloses substituted 4,5,6,7-tetrahydro-1H-imidazo[4,5 c]pyridine derivatives of the formula:

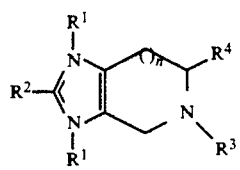

wherein— is a single or double bond; one of $R^1$ is present and includes groups such as $(CH_2)_{1-6}$naphthyl, $(CH_2)_{1-6}$heteroaryl, or $(CH_2)_{1-6}$Ph optionally substituted; $R^3$ includes groups such as $COC_{1-15}$alkyl or $(CH_2)_{1-6}$Ph optionally substituted; $R_4$ includes $CO_2R^9$, wherein $R^9$ is hydrogen, lower alkyl or benzyl; and n is 0–3. A compound specifically disclosed is 5-[(4-nitrophenyl)acetyl]-1-(phenylmethyl)-4,5,6,7-tetrahydro-1H-imidazo[4,5-c]pyridine-6-carboxylic acid.

European Patent Application 253,310 discloses substituted 1-aralkylimidazoles having the general formula:

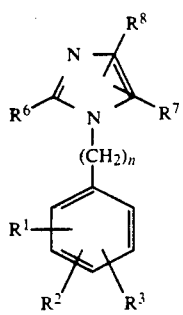

wherein $R^1$ includes groups such as phenyl optionally substituted or adamantylmethyl; $R^2$ includes groups such as hydrogen, halo, $NO_2$, $C_{1-4}$alkyl, or $C_{1-4}$alkoxy; $R^3$ is hydrogen, halo, $C_{1-4}$alkyl, or $C_{1-4}$alkoxy; $R^6$ includes groups such as $C_{2-10}$alkyl, $C_{3-10}$alkenyl, $C_{3-8}$cycloalkyl, benzyl optionally substituted or $Z(CH_2)_{1-5}$-$R^5$, wherein Z is O or S and $R^5$ is hydrogen, $C_{1-6}$alkyl, $C_{3-6}$cycloalkyl or alkenyl; $R^7$ is hydrogen, halo, $NO_2$, $CF_3$, or CN, and $R^8$ includes groups such as $C_{1-10}$alkanoic acids, esters and amides and alkyl N-alkyl carbamates. Examples include 2-n-butyl-5-chloro-1-(4-nitrobenzyl)imidazole-4-acetic acid and 1-[(2'-carboxybiphenyl-4-yl)methyl]-2-n-butyl-4-chloro-5-(dimethylcarbamoyl)imidazole.

Great Britain Patent 1,341,375 describes a series of substituted imidazoles which are useful due to their activity at H 1, H 2 and/or other histamine receptors. The substituted aminoalkylimidazole compounds disclosed therein are of the formula:

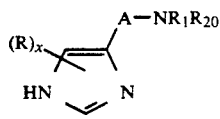

wherein A is $C_{1-6}$alkyl, optionally substituted by alkyl or aralkyl; R is a substituted or unsubstituted alkyl, aryl or aralkyl group; $R_1$ is hydrogen alkyl, phenyl, phenylalkyl or imidazolylalkyl; $R_{20}$ is hydrogen, alkyl optionally substituted by halo, OH, CN, $CO_2H$, $NH_2$ or $CONH_2$; or COY wherein Y is $R_{11}O$ or $R_{11}NH$ and $R_{11}$ is a substitued or unsubstituted alkyl, aryl, aralkyl or amidino qroup; and X is 0–3. Examples include N-(2-(4(5)-imidazolyl)ethyl)glycine and 1-benzyl-5-(2-aminoethyl) imidazole.

DESCRIPTION OF THE INVENTION

The compounds of the present invention that are blockers of angiotensin II receptors are represented by the following Formula (I):

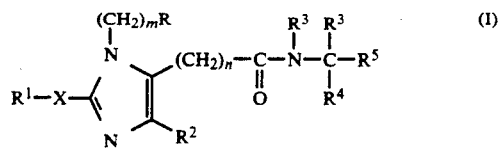

in which:

R is adamantyl, or naphthyl, biphenyl, or phenyl, with each aryl group being unsubstituted or substituted by one to three substituents selected from halo, $C_{1-6}$alkyl, $C_{1-6}$alkoxy, OH, CN, $CO_2R^3$, tetrazol-5-yl, $SO_3H$, $SO_2NHR^3$, $NO_2$, W, $SC_{1-6}$alkyl, $SO_2C_{1-6}$alkyl, $NHSO_2R^3$, $PO(OR^3)_2$, $NR^3R^3$, $NR^3COH$, $NR^3COC_{1-6}$alkyl, $NR^3CON(R^3)_2$, $NR^3COW$, or $SO_2W$;

$R^1$ is $C_{2-10}$alkyl, $C_{3-10}$alkenyl, $(CH_2)_{0-8}C_{3-6}$cycloalkyl, or $(CH_2)_{0-8}$phenyl unsubstituted or substituted by one to three substituents selected from $C_{1-6}$alkyl, $C_{1-6}$alkoxy, halo, OH, $NO_2$, $NR^3R^3$, W, $CO_2R^3$, CN, $CONR^3R^3$, $NR^3COH$, tetrazol-5-yl, $NR^3COC_{1-6}$alkyl, $NR^3COW$, $SC_{1-6}$Alkyl, $SO_2W$, or $SO_2C_{1-6}$alkyl;

X is a sinqle bond, S, $NR^3$, or O;

m is 0–4;

$R^2$ is H, $C_{1-6}$alkyl, halo, W, CHO, $CH_2OH$, $CO_2R^3$, $CONR^3R^3$, $NO_2$, CN, $NR^3R^3$, or phenyl;

each $R^3$ independently is H or $C_{1-6}$alkyl;

$R^4$ is H, $C_{1-8}$alkyl, thienyl-Y-, furyl-Y-, pyrazolyl-Y-, imidazolyl-Y-, thiazolyl-Y-, pyridyl-Y-, tetrazolyl-Y-, pyrrolyl-Y-, triazolyl-Y-, oxazolyl-Y-, isoxazolyl-Y-, or phenyl-Y-, with each aryl or heteroaryl group being unsubstituted or substituted by $C_{1-6}$alkyl, $C_{1-6}$alkoxy, halo, $NR^3R^3$, $CO_2R^3$, OH, $NO_2$, $SO_2NHR^3$, $SO_3H$, $CONR^3R^3$, W, $SO_2W$, $SC_{1-6}$alkyl, $SO_2C_{1-6}$alkyl, $NR^3COH$, $NR^3COW$, or $NR^3COC_{1-6}$alkyl;

$R^5$ $CO_2R^3$, $CONR^3R^3$, or tetrazol-5-yl;

W is $C_qF_{2q+1}$, wherein q is 1–4;

Y is a single bond or $C_{1-6}$alkyl which is straight or branched; and n is 0–5; or a pharmaceutically acceptable salt thereof.

Preferred compounds of the invention are represented by Formula (I) when:

R is phenyl unsubstituted or substituted by one to three substituents selected from chloro, fluoro, nitro, carboxy, trifluoromethyl, methyl, methoxy, hydroxy, sulfonamido, sulfamyl, cyano, carbo$C_{1-6}$alkoxy, carbamoyl, or tetrazol-5-yl;

$R^1$ is $C_{2-8}$alkyl;

X is a single bond or S;

m is 0, 1, or 2;

$R^2$ is hydrogen, chloro, fluoro, or trifluoromethyl;

each $R^3$ is independently hydrogen or methyl;

$R^4$ is hydrogen, $C_{1-4}$alkyl, phenyl-$(CH_2)_{0-2}$, or thienyl-$CH_2$;

$R^5$ is $CO_2R^3$ or tetrazol-5-yl; and n is 0–3; or a pharmaceutically acceptable salt thereof.

As used herein, the terms alkyl, alkenyl, alkoxy, and alkynyl mean carbon chains which are branched or unbranched with the length of the chain determined by the descriptor preceding the term. Included within the scope of Formula (I) compounds are the racemic mixtures as well as the single enantiomers encompassed by the genus of Formula (I).

Particular compounds of the invention include, but are not limited to, the following:

N-[{2-n-butyl-1-(2-chlorophenyl)methyl-1H-imidazol-5-yl}methylcarbonyl]-L-(2-thienyl)alanine;

N-[{2-n butyl-1-(2-chlorophenyl)methyl-1H-imidazol-5-yl}methylcarbonyl]-L-phenylalanine;

N-[{1-(2-chlorophenyl)methyl-2-propylthio-1H-imidazol-5-yl}methylcarbonyl]-L-phenylalanine;

N-[{2-n-butyl-1-(2-chlorophenyl)methyl-1H-imidazol-5-yl}methylcarbonyl]-glycine;

N-[{1-(2-chlorophenyl)methyl-2-propylthio-1H-imidazol-5-yl}methylcarbonyl]-L-homophenylalanine;

N-[{2-n-butyl-1-(2-chlorophenyl)methyl-1H-imidazol-5-yl}ethyl-2-carbonyl]-L-phenylalanine;

N-[{2-n-butyl-1-(2-chlorophenyl)methyl-1H-imidazol-5-yl}methylcarbonyl]-L-isoleucine;

N-[{1-(2-chlorophenyl)methyl-2-propylthio-1H-imidazol-5 yl}carbonyl]phenylalanine; and N-[{1-(2-chlorophenyl)methyl-2-propylthio-1H-imidazol-5 yl)carbonyl]glycine;

or a pharmaceutically acceptable salt thereof.

The invention also relates to pharmaceutical compositions comprising a pharmaceutical carrier and an effective amount of a compound of Formula (I).

Also included in the present invention are methods for antagonizing angiotensin II receptors which comprises administering to a subject in need thereof an effective amount of a compound of Formula (I). Methods of producing antihypertensive activity and methods of treating congestive heart failure, renal failure, and glaucoma by administering these compounds are also included in this invention.

The compounds of this invention and of the pharmaceutical compositions and methods of this invention are prepared by procedures described herein and illustrated by the examples. Reagents, protecting groups and functionality on the imidazole and other fragments of the molecule must be consistent with the proposed chemical transformations. Steps in the synthesis must be compatible with the functional groups and the protecting groups on the imidazole and other parts of the molecule.

The following procedures are useful for the preparation of Formula (I) particularly where R is 2-chlorophenyl or 4-carboxyphenyl, $R^1$ is n-propyl or n-butyl, m is one or two, X is S or a single bond, $R^2$ is hydrogen, chloro, or fluoro, each $R^3$ is hydrogen, $R^4$ is hydrogen, $C_{1-4}$alkyl, $(CH_2)_{0-2}$phenyl, or $CH_2$-2-thienyl, $R^5$ is $CO_2R^3$ or tetrazol-5-yl and n is 0-3.

Scheme 1

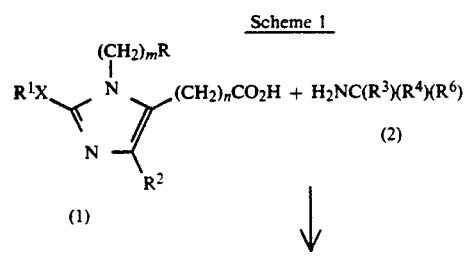

(1)

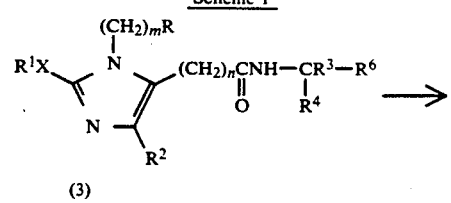

(3)

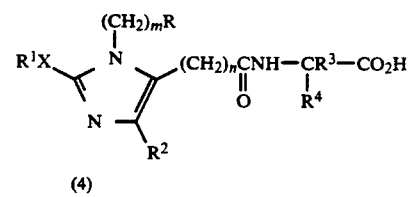

(4)

Scheme I shows the synthesis of Formula (I) compounds. The starting imidazole carboxylic acid compounds (1) are prepared, for example, by the procedures described in U.S. Pat. No. 4,340,598, dated Jul. 20, 1982. According to Scheme I, the acids (1) are reacted with formula (2) amino acid esters or α-aralkyl(1H-tetrazol-5-yl)methanamines [preparation described in J. Pharm. Sciences, 66:1642–1644 (177); in Scheme I, $R^6$ is $CO_2C_{1-6}$alkyl or 1H-tetrazol-5-yl] in the presence of a suitable amide-forming reagent, such as N hydroxysuccinimide or dicyclohexylcarbodiimide/1 hydroxybenzotriazole, in a suitable solvent, such as tetrahydrofuran or methylene chloride, to give the carboxamide compounds of formula (3) which are Formula (I) compounds in which $R^5$ is $CO_2C_{1-6}$alkyl or tetrazol-5-yl. The formula (3) imidazole esters are converted to the corresponding acids (4), for example by using a suitable aqueous base, such as aqueous potassium or sodium hydroxide in a $C_{1-4}$alkanol to give Formula (I) compounds in which $R^5$ is $CO_2H$.

Scheme II

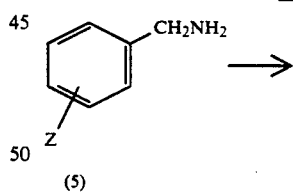

(5)

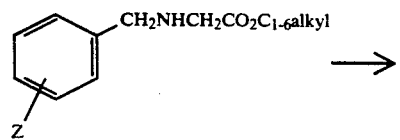

(6)

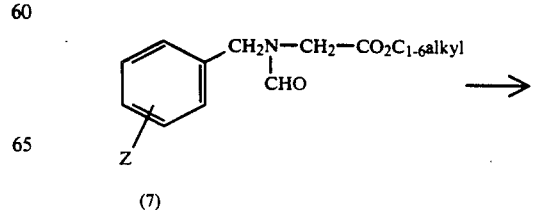

(7)

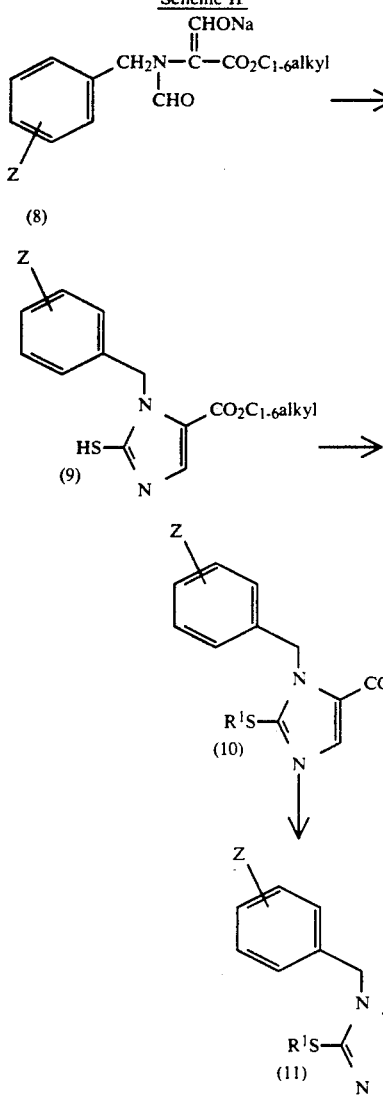

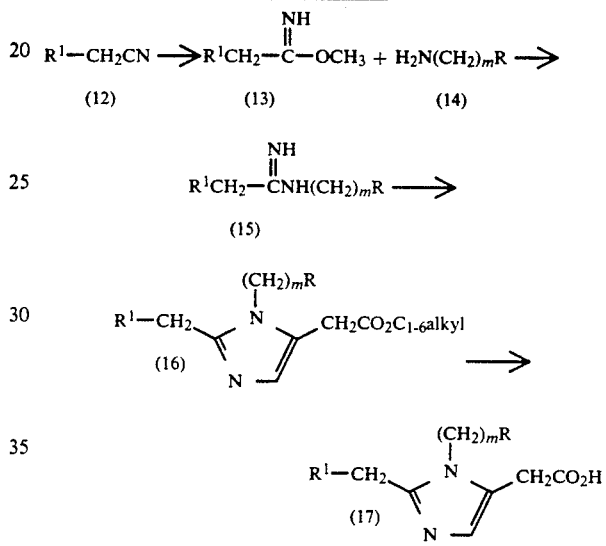

tuted $(CH_2)_{0-8}Ph$, preferably propyl bromide, in the presence of a suitable base, such as sodium carbonate, in an appropriate solvent, such as ethyl acetate, to give 1 $RCH_2$-2-$R^1S$-5-alkanoate ester imidazoles (10). The formula (10) ester compounds are converted to the corresponding acids (11), for example by using a suitable aqueous base, such as aqueous potassium or sodium hydroxide in a $C_{1-4}$alkanol. These 2-$R^1$ S-5-alkanoic acid imidazoles are then used as starting materials in the synthesis outlined in Scheme I to prepare Formula (I) compounds in which X is S, $R^2$ is H, $R^5$ is $CO_2R^3$ or tetrazol-5-yl, n is 0, m is one, and R, $R^1$, $R^3$, and $R^4$ are as defined in Formula (I).

Scheme II outlines the synthesis of Formula (I) compounds in which the 2 position substituent is $R^1S$. Benzylamines (5), substituted by one to three Z substituents selected from halo, $C_{1-6}$alkyl, $SO_2C_{1-6}$alkyl, $C_{1-6}$alkoxy, CN, $NO_2$, $CO_2C_{1-6}$alkyl, alkyl, or $C_qF_{2q+1}$, wherein q is 1–4, are alkylated with a $C_{1-6}$alkyl chloroacetate, for example methyl chloroacetate, in the presence of a base, such as triethylamine, in a suitable solvent, such as dimethylformamide. The resulting alkylaminoalkyl ester compounds (6) are N formylated with formic acid in the presence of a suitable solvent, such as xylenes, to give formula (7) compounds. Formula (8) compounds are formed by C formylation of the carbon alpha to both the amino and the ester groups of the formula (7) compounds in a reaction with an alkyl formate, such as methyl formate, in the presence of an alkali metal halide, such as sodium hydride, in a suitable solvent, such as tetrahydrofuran. Reaction of this intermediate with acidic thiocyanate, preferably potassium thiocyanate, in an inert organic solvent, such as $C_{1-4}$alkanol, produces 1-$RCH_2$-2-mercapto-5 alkanoate ester imidazoles (9). The free thio group of formula (9) compounds is reacted with a halo $R^7$ compound, wherein $R^7$ is $C_{2-10}$ alkyl, $C_{3-10}$, $(CH_2)_{0-8}C_{3-6}$cycloalkyl, or an optionally substi- Scheme III shows an alternate procedure for preparing imidazole acetic acid compounds, which are Scheme I, formula (1), compounds wherein n is 1. According to Scheme III, formula (12) nitrile compounds are converted to methyl alkylimidate compounds (13) for example by reacting the nitrile group with methanol in the presence of anhydrous hydrochloric acid. Formula (15) imido amine compounds are prepared by amination of formula (13) compounds with an appropriately substituted amine (14), such as 2 chlorobenzylamine, in a suitable solvent, such as tetrahydrofuran, at a temperature of 20° C. to 50° C., preferably at 25° C. The imidazoles of formula (16) are synthesized by reacting formula (15) compounds with $C_{1-6}$alkyl 3-formylacylates in a suitable solvent, such as tetrahydrofuran, at 25° C. to 100° C., preferably at 65° C. The formula (16) ester compounds are converted to the corresponding acids (17) for example by using a suitable aqueous base, such as aqueous potassium or sodium hydroxide in a $C_{1-4}$alkanol. These imidazole 5 acetic acid derivatives are then used as starting materials in the synthesis outlined in Scheme I to prepare Formula (1) compounds in which X is a single bond, $R^2$ is H, $R^5$ is $CO_2R^3$ or tetrazol-5-yl, n is 1, and R, $R^1$, $R^3$, $R^4$ and m are as defined in Formula (I).

Scheme IV

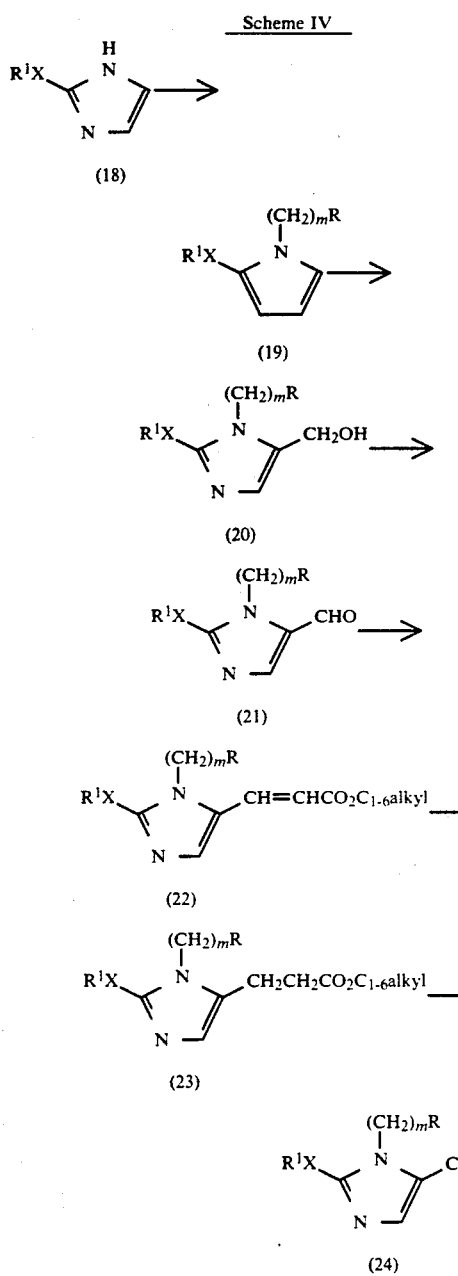

Scheme IV shows an alternate procedure for preparing imidazole 5-propionic acid derivatives, which are Scheme I, formula (1) compounds wherein n is 2.

The starting 2-$R^1$X-imidazoles (18) are known to the art (J. Org. Chem. 45:4038, 1980) or are synthesized by known procedures. For example, imidazole is converted to 2-n-butylimidazole by reacting imidazole with triethylorthoformate and p-toluenesulfonic acid to give 1 diethoxyorthoamide imidazole and then treating with n butyl lithium to give the 2-lithium derivative of the orthoamide and alkylating with n-butyl iodide in a suitable solvent, such as tetrahydrofuran (THF).

The 1-R(CH$_2$)$_m$-group is incorporated onto the 2-$R^2$X-imidazole (18) by known procedures, for example, by reaction with an R-(CH$_2$)$_m$ halide, mesylate or acetate, such as 2-chlorobenzyl bromide, in a suitable solvent, such as dimethylformamide (DMF), in the presence of a suitable acid acceptor, such as sodium alkylate, potassium or sodium carbonate, or a metal hydride, preferably sodium hydride at a reaction temperature of 25° C. to 100° C., preferably 50° C. The resulting 1-R(CH$_2$)$_m$-2-$R^1$X-imidazole (19) is hydroxymethylated in the 5-position, for example, by reacting with formaldehyde in the presence of sodium acetate in acetic acid to provide the 1-R(CH$_2$)$_m$-2-$R^1$X-5-hydroxymethylimidazole intermediates of formula (20).

The formula (20) hydroxymethyl group is oxidized to an aldehyde by treatment with a suitable reagent, such as anhydrous chromic acid-silica gel in tetrahydrofuran or, preferably with activated manganese dioxide, in a suitable solvent, such as benzene, toluene or, preferably methylene chloride, at a temperature of 25° C. to 140° C., preferably 25° C. These 1-R(CH$_2$)$_m$-2-$R^1$X-imidazol-5-carboxaldehyes (21) are reacted with an appropriate phosphonate, such as trimethylphosphonacetate. The reaction of the imidazol-5-carboxyaldehydes (21) with the phosphonates is performed in the presence of a suitable base, such as metal alkoxide, lithium hydride or, preferably, sodium hydride, in a suitable solvent, such as ethanol, methanol, ether, dioxane, tetrahydrofuran, or preferably glyme, at a reaction temperature of 10° C. to 50° C., preferably at 25° C., to provide a variable mixture of trans and cis, e.g., (E) and (Z), 1-$R^1$(CH$_2$)$_m$-2-$R^2$X-5-CH=C($R^5$)(COO-alkyl)imidazoles (22).

The double bond of the formula (22) imidazoles is reduced using catalytic hydrogenation to give formula (23) compounds. This reductive procedure is carried out in the presence of a suitable catalyst, such as platinum oxide or palladium on carbon, in a suitable solvent, such as C$_{1-4}$alkanol. The formula (23) ester compounds are converted to the corresponding imidazole 5 propionic acid derivatives (24) for example by using a suitable aqueous base, such as aqueous sodium or potassium hydroxide in a C$_{1-4}$alkanol. Formula (24) compounds are then used as starting materials in the synthesis outlined in Scheme I to prepare Formula (I) compounds in which, $R^2$ is H, $R^5$ is CO$_2$R or tetrazol-5-yl, n is 2 and R, $R^1$, $R^3$, $R^4$, X and m are as defined in Formula (I).

Scheme V

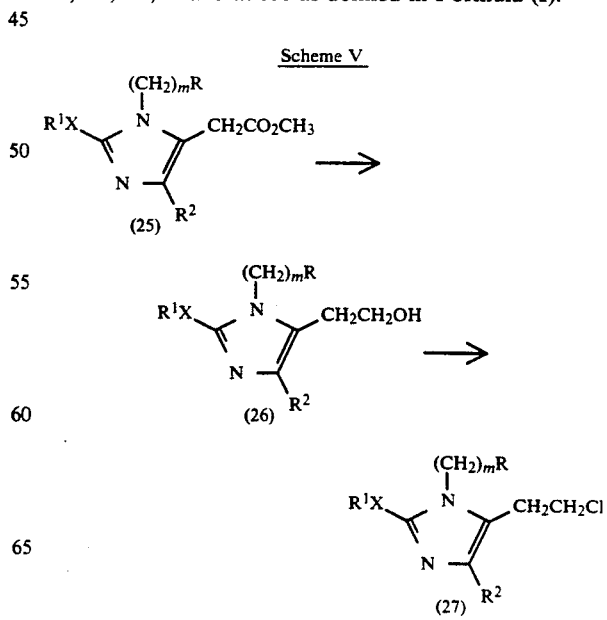

-continued
Scheme V

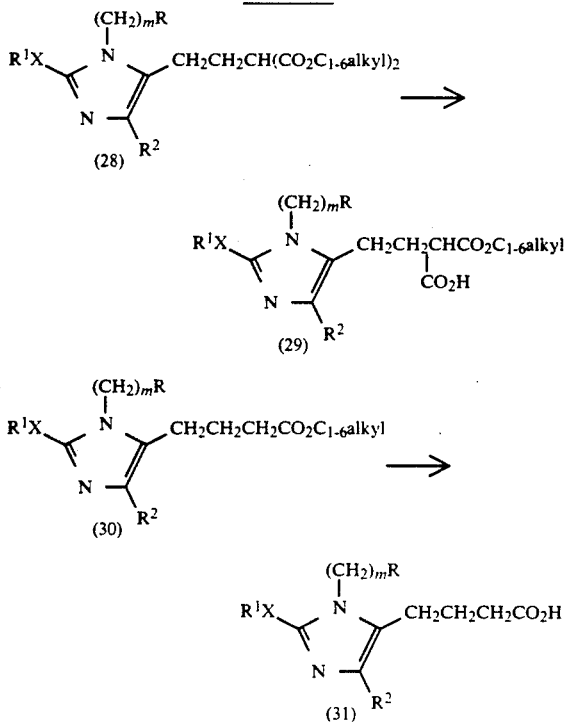

Scheme V shows the synthesis of Formula (I) compounds in which X is a single bond, $R^2$ is H, Cl, F, or $CF_3$, $R^5$ is $CO_2R^3$ or tetrazol-5-yl, n is 3, and R, $R^1$, $R^3$ and $R^4$ are as defined in Formula (I). According to Scheme V, imidazole acetic acid esters of formula (25) are reduced to the 5 hydroxyethylimidazoles (26) with a suitable reducing agent, such as diisobutylaluminum hydride, in a suitable solvent, such as tetrahydrofuran at a temperature of $-110°$ C. to 50° C. preferably $-78°$ C. to 25° C. Conversion of formula (26) compounds to the haloethyl compounds (27) takes place in a reaction with a halogenating agent, such as thionyl chloride, at a temperature of 25° C. to 79° C., preferably 79° C. Formula (28) compounds are formed by reacting formula (27) compounds with an alkali metal salt of a dialkylmalonate, such as sodium diethylmalonate. Partial hydrolysis of this diester intermediate with aqueous base in a $C_{1-4}$alkanol, such as aqueous sodium carbonate in ethanol, yields the half ester, half acid species of formula (29). Decarboxylation of formula (29) imidazoles by heating to 150° C. to 200° C., preferably 160° C., provides 5 butyric acid esters of formula (30). Hydrolysis of the ester qroup of formula (30) compounds to the corresponding acid compounds (31) is carried out using aqueous base in a $C_{1-4}$alkanol, such as aqueous sodium or potassium hydroxide in ethanol. Formula (31) compounds are then used as starting materials in the synthesis outlined in Scheme I to prepare formula (I) compounds in which n is 3.

Compounds of Formula (I) in which the R substituent is substituted by hydroxy are formed from Formula (I) compounds in which the R group is substituted by $C_1-C_6$alkoxy using an ether cleaving reagent, such as boron tribromide or hydrobromic acid.

Compounds of Formula (I) in which the R substituent is substituted by carboxy are formed from Formula (I) compounds in which the R group is substituted by $CO_2C_1-C_6$alkyl using basic hydrolysis, such as aqueous sodium or potassium hydroxide in methanol or ethanol, or using acidic hydrolysis, such as aqueous hydrochloric acid.

Formula (I) tetrazole compounds are prepared by the following procedure. The Formula (I) acid compounds, hereinbefore described, are reacted with a halogenating agent, such as thionyl chloride, in a suitable solvent, for example benzene, to give the corresponding acid halide compounds. The acid halides are then converted to primary amide compounds in a reaction with concentrated ammonia. Subsequent dehydration of the amides with oxalyl chloride/dimethylformamide in acetonitrile/dimethyl formamide yields the nitrile compounds, which are the immediate precursors to the Formula (I) tetrazole compounds. Tetrazole formation is accomplished by reacting the nitriles with azide, preferably aluminum azide prepared in situ by the reaction of sodium azide with aluminum chloride, in a suitable solvent, for example tetrahydrofuran.

Pharmaceutically acceptable acid addition salts of compounds of Formula (I) are formed with appropriate organic or inorganic acids by methods known in the art. For example, the base is reacted with a suitable inorganic or organic acid in an aqueous miscible solvent, such as ethanol, with isolation of the salt occurring by removal of the solvent or in an aqueous immiscible solvent when the acid is soluble therein, such as ethyl ether or chloroform, with the desired salt separating directly or isolated by removing the solvent. Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p aminobenzoic, glutamic, benzenesulfonic, hydrochloric, hydrobromic, sulfuric, cyclohexylsulfamic, phosphoric and nitric acids.

Pharmaceutically acceptable base addition salts of compounds of Formula (I) in which $R^5$ is $CO_2H$ are prepared by known methods from organic and inorganic bases, including non toxic alkali metal and alkaline earth bases, for example, calcium, lithium, sodium, and potassium hydroxide; ammonium hydroxide, and non toxic organic bases such as triethylamine, dicyclohexylamine, butylamine, piperazine, meglumine, choline, diethanolamine, and tromethamine.

Angiotensin II antagonist activity of the compounds of Formula (I) is assessed by in vitro and in vivo methods. In vitro antagonist activity is determined by the ability of the compounds to compete with $^{125}I$-angiotensin II for binding to vascular angiotensin II receptors and by their ability to antagonize the contractile response to angiotensin II in the isolated rabbit aorta. In vivo activity is evaluated by the efficacy of the compounds to inhibit- the pressor response to exogenous angiotensin II in conscious rats and to lower blood pressure in a rat model of renin dependent hypertension.

Binding

The radioligand binding assay is a modification of a method previously described in detail (Gunther et al., Circ. Res. 47:278, 1980). A particular fraction from rat mesenteric arteries is incubated in Tris buffer with 80 pM of $^{125}I$-angiotensin II with or without angiotensin II antagonists for 1 hour at 25° C. The incubation is terminated by rapid filtration and receptor bound $^{125}I$-angiotensin II trapped on the filter is quantitated with a gamma counter. The potency of angiotensin II antagonists is expressed as the $IC_{50}$ which is the concentration of antagonist needed to displace 50% of the total specifically bound angiotensin II. Exemplary of the $IC_{50}$ of compounds of the invention is about 1.5 to about 100 $\mu M$.

Aorta

The ability of the compounds to antagonize angio tensin II induced vasoconstriction is examined in the rabbit aorta. Ring segments are cut from the rabbit thoracic aorta and suspended in organ baths containing physiological salt solution. The ring segments are mounted over metal supports and attached to force displacement transducers which are connected to a recorder. Cumulative concentration response curves to angiotensin II are performed in the absence of antagonist or following a 30-minute incubation with antagonist. Antagonist dissociation constants ($K_B$) are calculated by the dose ratio method using the mean effective concentrations. Exemplary of the $K_B$ of compounds of the invention is about 0.3 to about 25 $\mu M$.

Inhibition of Pressor Response to Angiotensin II in Conscious Rats

Rats are prepared with indwelling femoral arterial and venous catheters and a stomach tube (Gellai et al., *Kidney Int.* 15:419, 1979). Two to three days following surgery the rats are placed in a restrainer and blood pressure is continuously monitored from the arterial catheter with a pressure transducer and recorded on a polygraph. The change in mean arterial pressure in response to intravenous injections of 250 mg/kg angiotensin II is compared at various time points prior to and following the administration of the compounds intravenously or orally at doses of 3 to 300 mg/kg. The dose of compound needed to produce 50% inhibition of the control response to angiotensin II ($IC_{50}$) is used to estimate the potency of the compounds. The $IC_{50}$ of N-[{2-n-butyl-1-(2-chlorophenyl)methyl-1H-imidazol-5-yl}methylcarbonyl-L-phenylalanine is 16 mg/kg.

Antihypertensive Activity

The antihypertensive activity of the compounds is measured by their ability to reduce mean arterial pressure in conscious rats made renin dependent hypertensive by ligation of the left renal artery (Cangieno et al., *J. Pharmacol. Exp. Ther.* 208:310, 1979). Renal artery ligated rats are prepared with indwelling catheters as described above. Seven to eight days following renal artery ligation, the time at which plasma renin levels are highest, the conscious rats are placed in restrainers and mean arterial pressure is continuously recorded prior to and following the administration of the compounds intravenously or orally. The dose of compound needed to reduce mean arterial pressure by 30 mm Hg ($IC_{30}$) is used as an estimate of potency.

The intraocular pressure lowering effects employed in this invention may be measured by the procedure described by Watkins, et al., *J. Ocular Pharmacol.*, 1 (2):161 168 (1985).

The compounds of Formula (I) are incorporated into convenient dosage forms, such as injectable preparations, or for orally active compounds, capsules or tablets. Solid or liquid pharmaceutical carriers are employed. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies but, preferably, will be from about 25 mg to about 1 g per dosage unit. When a liquid carrier is used, the preparation will be in the form of a syrup, elixir, emulsion, soft gelatin capsule, sterile injectable liquid, such as an ampoule, or an aqueous or nonaqueous liquid suspension.

For topical ophthalmologic administration, the pharmaceutical compositions adapted include solutions, suspensions, ointments, and solid inserts. Typical pharmaceutically acceptable carriers are, for example, water, mixtures of water and water-miscible solvents such as lower alkanols or vegetable oils, and water soluble ophthalmologically acceptable non toxic polymers, for example, cellulose derivatives such as methyl cellulose. The pharmaceutical preparation may also contain non toxic auxiliary substances such as emulsifying, preserving, wetting, and bodying agents, as for example, polyethylene glycols; antibacterial components such as quaternary ammonium compounds; buffering ingredients such as alkali metal chloride; antioxidants such as sodium metabisulfite; and other conventional ingredients such as sorbitan monolaurate.

In addition, suitable ophthalmic vehicles may be used as carrier media for the present purpose including conventional phosphate buffer vehicle systems.

The pharmaceutical preparation may also be in the form of a solid insert. For example, one may use a solid water soluble polymer as the carrier for the medicament. Solid water insoluble inserts, such as those prepared from ethylene vinyl acetate copolymer, may also be utilized.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral, parenteral, or topical products.

Doses of the compounds of Formula (I) in a pharmaceutical dosage unit as described above will be an efficacious, non-toxic quantity selected from the range of 0.01-200 mg/kg of active compound, preferably 0.1-100 mg/kg. The selected dose is administered to a human patient in need of angiotensin receptor antagonism from 1-6 times daily, orally, rectally, topically, by injection, or continuously by infusion. Oral dosage units for human administration preferably contain from 10 to 500 mg of active compound. Lower dosages are used generally for parenteral administration. Oral administration is used when safe, effective and convenient for the patient. Topical formulations contain the active compound in an amount selected from 0.0001 to 0.1 (w/v%), preferably 0.0001 to 0.01. As a topical dosage unit form, an amount of active compound from between 50 mg to 0.05 mg, preferably 50 mg to 5 mg is applied to the human eye.

The method of this invention of antagonizing angiotensin II receptors in mammals, including humans, comprises administering to a subject in need of such antagonism an effective amount of a compound of Formula (I). The method of this invention of producing antihypertensive activity and the methods of treating congestive heart failure, glaucoma, and renal failure comprise administering a compound of Formula (I) to a subject in need of the indicated activity in an effective amount to produce said activity.

The following examples illustrate preparation of compounds and pharmaceutical compositions of this invention. The examples are not intended to limit the scope of this invention as defined hereinabove and as claimed below.

Example 1

N-[{1-(2-Chlorophenyl)methyl-2-propylthio-1H-imidazol-5-yl}carbonyl]glycine

(i) 5 carboxymethyl-1-(2-chlorphenyl)methyl-2-thio-1H-imidazole

A solution of 2 chlorobenzylamine (14.2 g, 0.1 mol) and triethylamine (13.9 mL, 0.1 mol) in dimethylformamide (100 mL) was treated with methyl chloroacetate (10.9 q, 0.1 mol), and the mixture was heated at 50° C. for 3.5 hours. The cooled reaction mixture was diluted with ether, the solids filtered and the concentrated filtrate was flash chromatographed over silica gel with 6:4 hexane in ethyl acetate to provide 15.3 g (71%) of homogenous methyl 2-[N-(2-chlorophenyl)methyl]aminoacetate. This product (15.2 g, 0.071 mol) in mixed xylenes (100 mL) was treated with 98% formic acid (2.74 mL, 0.0711 mol) and the mixture was refluxed for 2.5 hours with a Dean Stark water separator. Evaporation gave 17.1 g (99%) of methyl 2-[N-(2-chlorophenyl)methyl-N-formyl]aminoacetate. This formylated product (17.0 g, 0.071 mol) was dissolved in methyl formate (13.3 mL, 0.215 mol) and added dropwise to a sodium methoxide mixture prepared by adding sodium metal (1.79 q, 0.0778 g atom) to tetrahydrofuran (325 mL) followed by slow addition of methanol (3.15 mL, 0.0778 mol). The combined mixture was stirred at room temperature for 17 hours, then evaporated to dryness. This crude product was dissolved in 50% aqueous methanol (200 mL), treated with charcoal, filtered and the solution was cooled in ice. Concentrated hydrochloric acid (14.3 mL of 12 N, 0.171 mol) was added slowly to this solution followed by a solution of potassium thiocyanate (8.6 g. 0.0884 mol) in water (20 mL). The mixture was heated in an oil bath held at 90° C. for 2.5 hours, then cooled to −10° C. The precipitated solid was filtered, washed with cold ethanol water and dried at 60° C to provide 14.7 g (74%) of 5-carboxymethyl-1-(2-chlorophenyl)methyl-2-thio-1H-imidazole; m.p. 72 74° C.

(ii) 1-(2-chlorophenyl)methyl-2-propylthio-1H-imidazole-5-carboxylic acid

A mixture of 5-carboxymethyl-1-(2-chlorophenyl)-methyl-2-thio-1H-imidazole (2 g, 7.08 mmol), ethyl acetate (20 mL), 5% sodium carbonate solution (40 mL) and propylbromide (4 mL, 44 mmol) was heated at 60° C. for 18 hours. The organic layer was separated, dried over magnesium sulfate and concentrated to 2.23 g of crude product. Trituration with ether provided 1.63 g (71% of 5-carboxymethyl-1-(2-chlorophenyl)methyl-2-propylthio-1H-imidazole; m.p. 68°–71° C. (from hexane). The ester was hydrolyzed with aqueous sodium hydroxide to give 1-(2-chlorophenyl)methyl-2-propylthio-1H-imidazole-5-carboxylic acid; m.p. 158°–159.5° C. (from ethanol).

(iii) N-[{1-(2-chlorophenyl)methyl-2-propylthio-1H-imidazol-5-yl}carbonyl]glycine] methyl ester A solution of 1-(2-chlorophenyl)methyl-2-thiopropyl-1H-imidazole-5-carboxylic acid (1.0 g, 3.22 mmol) in dry tetrahydrofuran (10 mL) was treated with N-hydroxysuccinimide (0.407 g, 3.54 mmol) followed by dicyclohexylcarbodiimide (0.664 g, 3.22 mmol). After being stirred for 1 hour at 25° C., qlycine methyl ester hydrochloride (0.525 g, 4.18 mmol) and triethylamine (0.58 mL, 4.18 mmol) were added and the mixture was stirred for 18 hours at 25° C. as dicyclohexyl urea precipitated. The urea was filtered, the filtrate concentrated to an oil and the crude product was passed through a flash column charged with silica gel. Elution with ethyl acetate provided a homogeneous product (TLC on silica gel with 3:2 ethyl acetate/hexane) as the low melting solid (1.08 g, 88%) N-[{1-(2-chlorophenyl)-methyl-2-propylthio-1H-imidazol-5-yl}carbonyl]glycine methyl ester.

(iv) N-[{1-(2-chlorophenyl)methyl-2-thiopropyl-1H-imidazol-5-yl}carbonyl]glycine To a solution of N-[{1-(2-chlorophenyl)methyl-2-propylthio-1H-imidazol-5-yl}carbonyl]glycine methyl ester (1.0 g, 2.62 mmol) in ethanol (20 mL) was added a solution of sodium hydroxide pellets (0.262 q, 6.55 mmol) in water (2 mL). The resulting solution was stirred at ambient temperature for 20 minutes. TLC on silica gel with 1:1 hexane/ethyl acetate and 9:1 methylene chloride/ methanol containing 2 drops of formic acid showed no starting material and one new product. The solution was acidified with dilute hydrochloric acid solution to pH 3.5, the product was concentrated to a white powder and this material was stirred with water and filtered. The title compound (0.535 g, 56%) was isolated as a white solid; mp 164°–166° C.

EXAMPLE 2

N-[{1-(2-Chlorophenyl)methyl-2-propylthio-1H-imidazol-5-yl}carbonyl]-L-alanine

The procedure of Example 1 (iii) was followed using L-alanine methyl ester hydrochloride (0.584 g, 4.18 mmol) in place of glycine methyl ester hydrochloride. The title compound, obtained after basic hydrolysis, was a white solid (345 mg, 28% for 2 steps); mp 173°–176° C. (from ethyl acetate/ethanol).

EXAMPLE 3

N-[1-(2-Chlorophenyl)methyl-2-propylthio-1H-imidazol-5-yl}carbonyl]-L-phenylalanine The procedure of Example 1 (iii and iv) was followed using L phenylalanine methyl ester hydrochloride in place of glycine methyl ester hydrochloride. The title compound was isolated as a solid; mp 178°–179° C. (from ethanol); $[\alpha]^{20}$ −46.0° (c=1, methanol).

EXAMPLE 4

N-[{1-(2-Chlorophenyl)methyl-2-propylthio-1H-imidazol-5-yl}carbonyl]-D-phenylalanine The procedure of Example 1 (iii and iv) was followed using D phenylalanine methyl ester hydrochloride in place of glycine methyl ester hydrochloride. The title compound was isolated as a solid; mp 176°–177° C.; [α] +44.5° (c=1, methanol).

EXAMPLE 5

N-[{1-(2-Chlorophenyl)methyl-2-propylthio-1H-imidazol-5-yl}carbonyl]-L-histidine The procedure of Example 1 (iii) was followed using L histidine methyl ester dihydrochloride in place of methyl ester hydrochloride. The intermediate N-[{1-(2-chlorophenyl)methyl-2-propylthio-1H-imidazole-5-yl}carbonyl]-L-histidine methyl ester was purified on a flash silica qel column with an elution solvent system of 9:1 ethyl acetate/methanol containing a trace of ammonium hydroxide to provide a 74% yield of the ester. The title compound, obtained after basic hydrolysis, was an off-white solid; mp 130°–131.5° C. (from ethanol/ethyl acetate/ether).

EXAMPLE 6

N-[{1-(2-Chlorophenyl)methyl-2-propylthio-1H-imidazol-5-yl}carbonyl]-L-isoleucine The procedure of Example 1 (iii) was followed using L-isoleucine methyl ester hydrochloride in place of glycine methyl ester hydrochloride. The intermediate N-[{1-(2-chlorophenyl)methyl-2-propylthio-1H-imidazol-5-yl}carbonyl]-L-isoleucine methyl ester was purified by flash column chromatography over silica gel with 7:3 hexane/ethyl acetate by flash column chromatoqraphy. The title compound, obtained after basic hydrolysis, was a solid; mp 156.5°–157.5° C. (from ethyl acetate/hexane).

EXAMPLE 7

N-[1-(2-Chlorophenyl)methyl-2-propylthio-1H-imidazol-5-yl}carbonyl]-L-tyrosine

The procedure of Example 1(iii) was followed using L-tyrosine methyl ester hydrochloride in place of glycine methyl ester hydrochloride. The intermediate N-[{1-(2-chlorophenyl)methyl-2-propylthio-1H-imidazol-5-yl}carbonyl]-L-tyrosine methyl ester was obtained as an oil in a 66% yield after column chromatography. The title acid was a white solid (60%); mp 180°–182° C. (from ethanol/ethyl acetate).

EXAMPLE 8

N-[{1-(2-Chlorophenyl)methyl-2-propylthio-1H-imidazol-5-yl}carbonyl]-α-methyl-DL-phenyalanine The procedure of Example 1 (iii and iv) was followed using α-methyl-DL-phenylalanine methyl ester hydrochloride in place of qlycine methyl ester hydrochloride. The title compound was a white solid; mp 167°–169° C. (from hexane/ethyl ether).

EXAMPLE 9

N-[{1-(2-Chlorophenyl)methyl-2-propylthio-1H-imidazol-5-yl}carbonyl]-L-phenylalanine (i)

N-[{1-(2-chlorophenyl)methyl-2-propylthio-1H-imidazol-5-yl}methyl-carbonyl]-L-phenylalanine methyl ester A solution of 2-[1-(2-chlorophenyl)methyl-2-propylthio-1H-imidazol-5-yl]acetic acid (0.52 g, 1.6 mmol) in tetrahydrofuran (20 mL) was stirred with N hydroxysuccinimide (0.203 g, 1.76 mmol) and dicyclohexylcarbodiimide (0.33 g, 0.16 mmol) for 30 minutes. Then L-phenylalanine methyl ester hydrochloride (0.449 g, 2.08 mmol) and triethylamine (0.21 g, 2.08 mmol) were added and the suspension was stirred at ambient temperature for 18 hours. The mixture was diluted with ethyl acetate, filtered and the concentrated filtrate was flash chromatographed over silica gel with 3:2 ethyl acetate/hexane to give 0.58 g (74%) of N-[{1-(2-chlorophenyl)methyl-2-propylthio-1H-imidazol-5-yl}methylcarbonyl]-L-phenylalanine methyl ester as an oil.

(ii)

N-[{1-(2-chlorophenyl)methyl-2-propylthio-1H-imidazol-5-yl}methylcarbonyl]-L-phenylalanine The methyl ester from Example 9 (i) (0.58 g, 1.2 mmol) was dissolved in ethanol (10 mL) and a solution of potassium hydroxide (0.223 g, 4 mmol) in water (4 mL) was added. This solution was stirred at room temperature for 1.5 hours. The ethanol was evaporated, the residue was diluted with water (10 mL) and the basic solution was extracted with ether. The aqueous layer was acidified to pH 3.5 with 10% hydrochloric acid solution, and the cooled suspension was then filtered, washed with water and dried in vacuum to provide 0.46 g (82%) of N-[1-(2-chlorophenyl)methyl-2-propylthio-1H-imidazol-5-yl}methylcarbonyl]-L-phenylalanine; mp 120°–121° C.

EXAMPLE 10

N-[{1-(2-Chlorophenyl)methyl-2-propylthio-1H-imidazol-5-yl}propyl-3-carbonyl]-L-phenylalanine (i)

Ethyl-4-[1-(2-chlorophenyl)methyl-2-propylthio-1H-imidazol-5yl]butyrate

A solution of methyl 2-[1-(2-chlorophenyl)methyl-2-thiopropyl-1H-imidazol-5-yl]acetate (2.1 g, 6.2 mmol) in dry tetrahydrofuran (150 mL) was cooled to −78° C. under an atmosphere of argon, and diisobutylaluminum hydride (17.5 mL of 1 M in toluene, 17.5 mmol) was added dropwise. After the addition was complete, the temperature was allowed to reach ambient temperature and was then stirred for 18 hours. Methanol was added cautiously followed by the addition of water and dilute acetic acid. The mixture was concentrated in vacuo, the product extracted into methylene chloride and the organic layer was washed with water, 5% sodium carbonate solution and brine. The dried, concentrated product was chromatographed over silica gel using ethyl acetate as the eluent to provide 1.6 g (84%) of 1-(2-chlorophenyl)methyl-5-(2-hydroxyethyl)-2-propylthio-1-H-imidazole. This product (0.602 g) was dissolved in thionyl chloride (6 mL), stirred for 0.5 hours at 25° C. and then heated to reflux for 0.5 hours. The solvent was evaporated, and the residue azeotroped with toluene (3×). Ether was added to the crude product to give a precipitate (9.63 g, 89%) of 5-(2-chloroethyl)-1-(2-chlorophenyl) methyl-2-propylthio-1H-imidazole-hydrochloride; mp 135°–136° C.

The above hydrochloride was converted to the free base in ether with 5% sodium bicarbonate solution. To a suspension of sodium hydride (57 mg, 2.38 mmol) in dimethylformamide (3 mL) held at 0° C. under argon was added a solution of diethyl malonate (0.4 g, 2.5 mmol) in dimethylformamide (3 mL). The mixture was stirred at ambient temperature for 0.5 hour or until a clear solution resulted. Then, 5-(2-chloroethyl)-1-(2-chlorophenyl)methyl-2-propylthio-1H-imidazole (0.61 g, 1.85 mmol) in dimethylformamide (5 mL) was added, and the mixture was heated at 95° C.–100° C. for 24 hours. The reaction was partitioned between water and ethyl acetate, and the organic layer was washed with water, dried, concentrated and the residue chromatographed to provide 0.6 q (71%) of diethyl 2-[1-(2-chlorophenyl)methyl-2-propylthio-1H-imidazol-5-yl]ethylmalonate as an oil.

This product (0.35 g, 0.773 mmol) was dissolved in ethanol (30-mL) and a solution of sodium carbonate (1.23 g, 11.6 mmol) in water (20 mL) was added. The mixture was stirred at 25° C for 78 hours, poured into water and extracted with ether. The aqueous layer was acidified to pH 3.5 with dilute hydrochloric acid solution, the product was extracted into ethyl acetate and the washed, dried and concentrated product (0.272 g) was decarboxylated without further purification.

This mono-acid mono-ester was heated in an oil bath at 160° C. for 2 hours. The residue was chromatographed over silica qel with a gradient of methanol in methylene chloride to give 0.110 g of ethyl 4-[1-(2-chlorophenyl)methyl-2-propylthio-1H-imidazol-5-yl]butyrate.

(ii)
4-[1-(2-chlorophenyl)methyl-2-propylthio-1H-imidazol-5-yl]butyric acid

A solution of ethyl 4-[1 (2-chlorophenyl)methyl-2-propylthio-1H-imidazol-5-yl]butyrate (244 mg) was dissolved in ethanol (5 mL) and a solution of potassium hydroxide (950 mg) in water (5 mL) was added. After being stirred at room temperature for 2 hours, the solution was diluted with water, acidified to pH 3.5 to 4.0 with 10% hydrochloric acid solution and the precipitated product was filtered, washed well with water and recrystallized from acetonitrile to afford 0.144 g (64%) of 4-[1-(2-chlorophenyl)methyl-2-propylthio-1H-imidazol-5-yl]butyric acid; mp 98°-99° C.

(iii)
N-[{1-(2-chlorophenyl)methyl-2-propylthio-1-H-imidazol-5-yl}propyl-3-carbonyl]-L-phenylalanine methyl ester The procedure of Example 9 (i) was followed using 4-[1-(2-chlorophenyl)methyl-2-propylthio-1H-imidazol-5-yl]butyric acid in place of 2-[1-(2-chlorophenyl)methyl-2-propylthio-1H-imidazol-5-yl}acetic acid. After chromatography on silica gel with ethyl acetate as the eluant, the title compound was obtained as an oil in a 94% yield.

(iv)
N-[{1-(2-chlorophenyl)methyl-2-propylthio-1H-imidazol-5-yl}propyl3-carbonyl]-L-phenylalanine The procedure of Example 9 (ii) was followed using N-[{1-(2-chlorophenyl)methyl-2-propylthio-1H-imidazol-5-yl}propyl-3-carbonyl]-L-phenylalanine methyl ester in place of N-[{1-(2-chlorophenyl)methyl-2-propylthio-1H-imidazole-5-yl}methylcarbonyl-L-phenylalanine methyl ester. The title compound was an amorphous solid; mp 94°-98° C.

EXAMPLE 11

N-[2-n-Butyl-1-(2-chlorophenyl)methyl-1H-imidazol-5-yl}ethyl-2-carbonyl]-L-phenylalanine (i) methyl 3-[2-n-butyl-1-{(2-chlorophenyl)methyl-1H-imidazole (a) 2 n butyl 1 (2 chlorophenyl)methyl-1H-imidazole Imidazole was converted to the 1 diethyoxyortho amide derivative by the method of Curtis and Brown, *J. Org. Chem.*, (1980), 45, 20. Imidazole (12.8 g, 0.19 mol) and 118.4 g (0.8 mol) of triethylorthoformate were reacted in the presence of 1 g of p toluenesulfonic acid to give 20.6 (61%), bp 65°-70° C. (0.1 mm) of 1-diethoxyorthoamide imidazole. This product (24.0 g, 0.14 mol) was dissolved in dry tetrahydrofuran (250 mL), cooled to −40° C. and n-butyl lithium (0.14 mol, 56.4 mL of 2.5 M in hexane was added at −40° C. to −35° C. After 15 minutes n butyl iodide (31.1 g, 0.169 mol) was added at −40° C., and the reaction was stirred overnight at ambient temperature. The reaction was partitioned between ether and 0.3 N hydrochloric acid, and the organic layer was repeatedly extracted with dilute hydrochloric acid. The combined aqueous extracts were neutralized with sodiuum bicarbonate solution, extracted with methylene chloride, dried over magnesium sulfate and concentrated. A flash distillation on a Kugelrohr apparatus provided 14.8 g (85%) of 2-n-butylimidazole.

2-n-Butylimidazole (9.7 g, 0.078 mol) was dissolved in methanol (50 mL) and added- dropwise to a solution of sodium methoxide [from sodium hydride (2.31 q, 0.0934 mol) in methanol (250 mL)]. After one hour the solution was evaporated to dryness, and the sodium salt was taken up in dimethylformamide (150 mL) and 2-chlorobenzylbromide (16.3 g, 0.079 mol) was added. The mixture was heated at 50° C. for 17 hours under argon, poured onto ice water and the product was extracted into ethyl acetate. The extract was washed, dried, and concentrated to give 18.5 g of crude product which was chromatographed over silica gel with 2:1 ethyl acetate/hexane to provide 11.9 g (61%) of 2-n-butyl-19(2-chlorophenyl)methyl-1H-imidazole as an oil. Thin layer chromatography on silica gel with 4:1 ethyl acetate/hexane gave a product with an Rf value of 0.59.

(b) 2 n butyl 1 (2-chlorophenyl)-5-hydroxy-methyl-1H-imidazole

Method A:

A mixture of 2-n-butyl-1-(2-chlorophenyl)-methyl-1H-imidazole (95.5 g, 01.384 mol), 37% formaldehyde (500 mL), sodium acetate (80 g) and acetic acid (60 mL) was heated to reflux for 40 hours under argon. The reaction was concentrated in vacuo, and the residue was stirred with 500 mL of 20% sodium hydroxide solution for 4 hours, diluted with water and extracted with methylene chloride The extract was washed, dried, and concentrated. The crude product (117 g) was flash chromatographed over 600 g of silica gel with a gradient of from 100% ethyl acetate to 10% of methanol in ethyl acetate to give 8.3 g of starting material, 24.5 g of mixture of starting material and product, and 44 g (41%) of 2-n-butyl-1-(2-chlorophenyl)methyl-5-hydroxymethyl-1H-imidazole; mp 86°-88° C. (from ethyl acetate). Further elution provided the bis (4,5 hydroxymethyl) derivative; mp 138°-140° C. (from ethyl acetate).

Method B:

A mixture of valeramidine methyl ether hydrochloride (250 q, 1.66 mol) and dihydroxyacetone (150 g, 0.83 mol) dissolved in liquid ammonia was allowed to stand overnight at room temperature in a pressure vessel, and then heated at 65° C. for 4 hours at 375 psi. The ammonia was allowed to evaporate, and the residue was dissolved in methanol (3 L). The resulting slurry was refluxed with added acetonitrile (1 L). The solution was decanted from the solid ammonium chloride while hot. This procedure was repeated, and the combined acetonitrile extracts were treated with charcoal, filtered hot and the filtrate was concentrated in vacuum to give the dark oil, 2-n-butyl-5-hydroxymethylimidazole (253 g, 1.63 mol, 98%).

This crude alcohol (252 g) was treated with acetic anhydride (400 mL) at −15° C. and then was allowed to warm to ambient temperature with stirring, and then stirred an additional 19 hours. The acetic anhydride was evaporated at reduced pressure, the residue taken up in methylene chloride, and the organic phase was washed with 5% sodium bicarbonate solution and water. The extract was dried over sodium sulfate and concentrated to give 323 q (83%) of 1-acetoxy-4-acetoxymethyl-2-n-butylimidazole.

This diacetate was N-alkylated by the following procedure. To a solution of triflic anhydride (120 mL, 0.71 mol) in methylene chloride (200 mL) at −78° C. under argon was added a solution of diisopropyl ethylamine (128 mL, 0.73 mol) and 2-chlorobenzyl alcohol (104 g, 0.72 mol) in methylene chloride (350 mL) over a period of 20 minutes. After being stirred an additional 20 minutes at −78° C., this solution was then treated with 1-acetoxy-4-acetoxymethyl-2-n-butylimidazole (146 g, 0.61 mol) dissolved in methylene chloride (300 mL) over a 20 minute interval. The mixture was then stirred at ambient temperature for 18 hours and the solvents were evaporated.

The residual 2-n-butyl-5-acetoxymethyl-1-(2-chlorophenyl)methyl-1H-imidazole was used without purification for the hydrolysis of the acetate group.

A solution of crude 2 n butyl-5-acetoxymethyl-1-(2-chlorophenyl)methyl-1H-imidazole (250 g) in methanol (200 mL) was treated with 10% sodium hydroxide solution (700 mL) and the mixture was heated on a steam bath for 4 hours. After cooling, methylene chloride was added, the organic phase was separated, washed with water, dried and concentrated. The residue was dissolved in ether, cooled and seeded to give the crude product. Recrystallization from ethyl acetate gave 176 g of 2-n-butyl-1-(2-chlorophenyl)methyl-5-hydroxymethyl-1H-imidazole; mp 86°-88° C. This material was identical in all respects to the product prepared by Method A.

(c) 2-n-butyl-1-(2-chlorophenyl)methyl-1H-imidazole-5-carboxaldehyde

A solution of 2-n-butyl-1-(2-chlorophenyl)methyl-5-hydroxymethyl-1H-imidazole (5.4 g, 0.0194 mol) in toluene (25 mL) was added to a suspension of activated manganese dioxide (27 g) in toluene (325 mL) which was previously concentrated with a Dean Stark water separator at reflux for one hour. The suspension was heated at 100° C. for 17 hours. The solids were filtered and the filtrate concentrated and flash chromatographed over silica gel with 6:4 hexane/ethyl acetate to afford 4.16 g (78%) of 2-n-butyl-1-(2-chlorophenyl)-methyl-1H-imidazole-5-carboxaldehyde as an oil. NMR and IR were consistent with the structure.

(d) methyl-[2-n-butyl-1-{(2-chlorophenyl)methyl}-1H-imidazol-5-yl]-2-propenoate

To a suspension of sodium hydride (0.492 g, 0.0205 mol) in glyme (30 mL) was added dropwise under argon trimethyl phosphonoacetate (3.73 g, 0.0205 mol). After one hour at ambient temperature, 2-n-butyl-1-{(2-chlorophenyl)methyl}-1H-imidazol-5-carboxaldehyde (3.78 g, 0.0137 mol) was added, and the mixture was stirred at 40° C. for one hour. The reaction was quenched with ice water, the product extracted into ether and the washed, dried concentrated product slowly crystallized to the low melting solid (3.39 g, 83%) methyl (E)-3-[-2-n-butyl-1-{(2-chlorophenyl)methyl}-1H-imidazole-5-yl]-2-propenoate.

(ii) N-[{2-n-butyl-1-(2-chlorophenyl)methyl-1H-imidazol-5-yl}ethyl-2-carbonyl]-L-phenylalanine methyl ester Methyl-3-[2-n-butyl-1-[(2-chlorophenyl)methyl}-1H-imidazol-5-yl]-2-propenoate (324 mg, 0.973 mmol) was dissolved in ethanol (10 mL), platinum oxide (35 mg) was added and the suspension was stirred under an atmosphere of hydrogen for 1.5 hours. The catalyst was flitered and the filtrate was concentrated to 313 mg (96%) of methyl-3-[2-n-butyl-1-{(2-chlorophenyl)methyl}1H-imidazol-5-yl]propanoate as an oil.

A solution of this ester (313 mg, 0,935 mmol) in ethanol (8 mL) was treated with a solution of sodium hydroxide (112 mg, 2.8 mmol) in water (3 mL), and the solution was stirred at ambient temperature for 1.5 hours. The ethanol was evaporated, 10% hydrochloric acid was added to pH 1.5 and the precipitated solid was filtered and washed with cold water and then with ether. The vacuum dried white solid (225 mg, 67%) was the hydrochloride salt of 3-[2-n-butyl-1-{(2-chlorophenyl)methyl}-1H-imidazol-5-yl]propanoic acid; mp 163.5°–164.5° C.

Following the procedure of Example 1(iii) using 215 mg (0.602 mmol) of 3-[2-n-butyl-1-((2-chlorophenyl)-methyl}-1H-imidazol-5-yl]propanoic acid and 69 mg (0.782 mmol) of L-phenylalanine methyl ester hydrochloride was obtained 420 mg of crude product. This was dissolved in ethyl acetate, applied to a flash chromatography column packed with silica gel, and eluted with a gradient from 100% ethyl acetate to 10% methanol in ethyl acetate to provide 270 mg (93%) of N-[{2-n-butyl-1-(2-chlorophenyl)methyl-1H-imidazol-5-yl}ethyl-2-carbonyl]-L-phenylalanine methyl ester (ii) N-[{2-n-butyl-1-(2-chlorophenyl)methyl-1H-imidazol-5-yl}ethyl-2-carbonyl]-L-phenylalanine The procedure of Example 1-(iv) was followed using L N-[{2-n-butyl-1-(2-chlorophenyl)methyl-1H-imidazol-5-yl}ethyl-2-carbonyl]-L-phenylalanine methyl ester (290 mg, 0.602 mmol) in place of N-[{1-(2-chlorophenyl)methyl-2-propylthio-1H-imidazol-5-yl}carbonyl]glycine methyl ester. The title compound was obtained in 69% yield; mp 85°-88° C.

EXAMPLE 12

N-[{2-n-Butyl-1-(2-chlorophenyl)methyl1H-imidazol-5-yl-methylcarbonyl]glycine (i) 2-[2-n-butyl-1-[(2-chlorophenyl)methyl}-1H-imidazol-5-yl]acetic acid A suspension of methyl pentylimidate hydrochloride (prepared from pentyl nitrile, methanol and anhydrous hydrochloric acid) (28.3 g, 0.187 mol) in anhydrous ethyl ether (500 mL) was treated with triethylamine (25 mL, 0.179 mol). The mixture was stirred under argon at ambient temperature for 24 hours. The solids were filtered, the filter cake washed with ether and the filtrate was concentrated in vacuo to give 18.45 g (86%) of methyl pentylimidate. This was used immediately in the next reaction.

A solution of methyl pentylimidate (18.45 g, 0.16 mol) in tetrahydrofuran (100 mL) was treated dropwise over 20 minutes with a solution of 2-chlorobenzylamine (22.7 g, 0.16 mol) in tetrahydrofuran (100 mL). This mixture was heated on a steam bath for 24 hours under argon. The solvent was removed in vacuo and excess 2-chlorobenzyl amine was removed at 80° C. under high vacuum. An NMR of the product showed pure N-(2-chlorobenzyl)pentylamidine (29.15 g, 81%).

A solution N (2-chlorobenzyl)pentylamidine (29.15 g, 0.13 mol) in tetrahydrofuran (100 mL) was added over 30 minutes to a stirred solution of ethyl-3 formyl acrylate (18.28 g, 0.143 mol) in tetrahydrofuran (500 mL). After the initial exothermic reaction, the mixture was stirred at 25° C. for 1 hour, refluxed on the steam bath for 4 hours and then concentrated to a mixture of predominently ethyl 2-[2-n-butyl-1-{(2-chlorophenyl)-methyl}-1H-imidazol-5-yl]-acetate and a small amount of the isomeric ethyl-2-[2-n-butyl-1-(2-chlorophenyl)-methyl}-1H-imidazol-4-yl]-acetate. This mixture of esters was dissolved in methanol (200 mL) and a 10% solution of sodium hydroxide in water (600 mL) was added. The reaction was refluxed for 5 hours. The methanol was removed in vacuo, the concentrated product was diluted with water (150 mL) and then the aqueous phase was extracted several times with ether and acidified to pH 1 with concentrated hydrochloric acid. The mixture was washed with ether, then with ethyl acetate. The aqueous phase was saturated with sodium chloride and then extracted with chloroform. The organic extracts were washed with brine, dried, and concentrated to 31.4 g of a crude product. Acetone (50 mL) was added with warming, the solution was cooled and the precipitated crystals were filtered, washed with cold acetone and dried to provide 19.54 g (44%) of 2-[2-n-butyl-1-{(2-chloro phenyl)methyl}-1H-imidazole-5-yl]acetic acid hydrochloride; mp 165°-167° C. The filtrate on evaporation provided 8.76 g of a 1:1 mixture of the 4- and 5- isomeric acetic acid derivatives (TLC on silica gel with 8.5/1.5 chloroform/methanol containing a trace of formic acid).

(ii) N-[{2 n butyl 1-(2-chlorophenyl)methyl}-1H-imidazol-5-yl}methylcarbonyl]glycine methyl ester The procedure of Example 1-(iii) was followed using 0.5 g (1.63 mmol) of 2-[2-n-butyl-1-{(2-chlorophenyl)-methyl}-1H-imidazol-5-yl]acetic acid, 0.21 g (1.79 mmol) of N-hydroxysuccinimide, 0.37 g (1.79 mmol) of dicyclohexylcarbodiimide, 0.27 g (2.12 mmol) of glycine methyl ester hydrochloride, triethylamine (0.3 mL, 2.12 mmol) and methylene chloride (15 mL), there was obtained 0.33 g (53%) of N-[{2-n-butyl-1-(2-chlorophenyl)methyl-1H-imidazol-5-yl}methylcarbonyl]glycine methyl ester as an oil.

(iii)
N-[{2-n-butyl-1-(2-chlorophenyl)methyl}-1H-imidazol-5-yl}methylcarbonyl]glycine The compound was prepared according to the procedure of Example 1-(ii) using N-[{2-n-butyl-1-(2-chlorophenyl)methyl-1H-imidazol-5-yl}methylcarbonyl]glycine methyl ester in place of N-[{1-(2-chlorophenyl)-methyl-2-propylthio-1H-imidazol-5-yl}carbonyl]glycine methyl ester. The title compound is an off white solid, and was obtained in 73% yield; mp 84°-88° C. (hydrochloride salt).

EXAMPLE 13

N-[{-2-n-Butyl-1-(2-chlorophenyl)methyl-1H-imidazol-5-yl}methylcarbontl-L-2-phenylglycine The procedure of Example 12 (ii–iii) was followed using L-phenylglycine methyl ester hydrochloride in place of glycine methyl ester hydrochloride. The intermediate N-[{2-n-butyl-1-(2-chlorophenyl)methyl-1H-imidazol-5-yl}methylcarbonyl]-L-2-phenylglycine methyl ester was flash chromatographed on silica gel with 90:10 methylene chloride/methanol in 95% yield to give an oil which slowly crystallized to a low melting solid. After hydrolysis of the ester with aqueous methanolic sodium hydroxide, the title compound was isolated as a white solid in a 59% yield; mp 163°-166° C. (from methanol/ethyl acetate).

EAXMPLE 14

N-[{2-n-Butyl-1-(2-chlorophenyl)methyl-1H-imidazol-5-yl}methylcarbonyl]-L-phenylalanine The procedure of Example 12 (ii–iii) was followed using L-phenylalanine methyl ester hydrochloride in place of glycine methyl ester hydrochloride. From 5.59 g (16.3 mmol) of 2-[2-n-butyl-1-{(2-chlorophenyl)methyl}-1H-imidazol-5-yl]acetic acid hydrochloride, there was obtained 6.88 g (90%) of the intermediate N-[{2-n-butyl-1-(2-chlorophenyl)methyl-1H-imidazol-5-yl}methylcarbonyl]-L-phenylalanine methyl ester; mp 88°-90° C. (from ethanol/water). Hydrolysis of this ester provided the title compound in a 79% yield; mp 168°-170° C.; $[\alpha]^{25}$ (c=1, methanol).

EXAMPLE 15

N-[{2-n-Butyl-1-(2-chlorophenyl)methyl-1H-imidazol-5-yl}methylcarbonyl]-D-phenylalanine The procedure of Example 12 (ii–iii) was followed using D-phenylalanine methyl ester hydrochloride in place lycine methyl ester hydrochloride. The intermediate N-[{2-n-butyl-1-(2-chlorophenyl)methyl-1H-imidazol-5-yl}methylcarbonyl]-D-phenylalanine methyl ester was a solid; mp 179°-181° C. (from methanol/ethyl acetate). The title compound was a solid; mp 178°-181° C. (from methanol/ethyl acetate).

EXAMPLE 16

N-[{2-n-Butyl-1-(2-chlorophenyl)methyl-1H-imidazol-5-yl}methylcarbonyl]-DL-homophenylalanine The procedure of Example 12 (i–iii) was followed using DL-homophenylalanine methyl ester hydrochloride in place of glycine methyl ester hydrochloride. From 1.0 g (3.26 mmol) of 2-[2-n-butyl-1 [(2-chlorophenyl)methyl}1H-imidazol-5-yl]acetic acid hydrochloride, there was obtained 1.53 g (97%) of the intermediate N-[{2-n-butyl-1-(2-chlorophenyl)methyl-1H-imidazol-5-yl}methylcarbonyl[-DL-homophenylalanine methyl ester. The title compound was isolated, after basic hydrolysis of the precursor ester, as the hydrochloride salt; mp 119-120° C.

EXAMPLE 17

N-[{2-n-Butyl-1-(2-Chlorophenyl)methyl-1H-imidazol-5-yl}methylcarbonyl]-DL-hydrocinnamic acid The procedure of Example 12 (ii–iii) was followed using DL-β-hydrocinnamic acid methyl ester hydrochloride in place of glycine methyl ester hydrochloride. From 1.0 g (2.91 mmol) of 2-[2-n-butyl-1-{(2-chlorophenyl)methyl}1H-imidazol-5-yl]acetic acid hydrochloride, there was obtained 0.92 g (68%) of the intermediate N-[{2-n butyl-1-(2-chlorophenylmethyl-1H-imidazol-5-yl}-methylcarbonyl]-DL-β-hydrocinnamic acid methyl ester. The title compound was isolated after basic hydrolysis of the ester in 70% yield as the hydrochloride salt; mp 208°-210° C. (from methanol/ethyl acetate).

EXAMPLE 18

N-[{2-n-Butyl-1-(2-chlorophenyl)methyl-1H-imidazol-5-yl}methylcarbonyl]-L-(2-thienyl)alanine The procedure of Example 12 (ii–iii) was followed using L-(2-thienyl)alanine methyl ester hydrochloride in place of glycine methyl ester hydrochloride. The intermediate N-[{2-n-butyl-1-(2-chlorophenyl)methyl-1H-imidazol-5-yl}methylcarbonyl]-L-(2-thienyl)alanine methyl ester was a solid; mp 66°-69° C. (from ethanol/water). Basic hydrolysis of this ester by the standard procedure [Example 1-(iv)]provided the title compound; mp 122°-125° C. (from ether trituration).

EXAMPLE 19

N-[[2-n-Butyl-1-(2-chlorophenyl)methyl-1H-imidazol-5-yl}methylcarbonyl]-L-isoleucine The procedure of Example 12 (ii–iii) was followed using L isoleucine methyl ester hydrochloride in place of glycine methyl ester hydrochloride. The title compound was isolated as the hydrochloride salt; mp 163°-166° C. (from ethyl acetate/ether); $[\alpha]^{25}$ −2.27° C. (c=1, methanol).

EXAMPLE 20

N-[{2-n-Butyl-1-(2-chlorophenyl)methyl-1H-imidazol5-yl}methylcarbonyl]-DL-α-methyl-phenylalanine The procedure of Example 12 (ii–iii) is followed using DL-α-methylphenylalanine methyl ester hydrochloride in place of glycine methyl ester hydrochloride to give the title compound.

EXAMPLE 21

N-[{2-n Butyl-1-(2-chlorophenyl)methyl-1H-imidazol-5-yl}methylcarbonyl]-N-methyl-L-phenylalanine The procedure of Example 12 (ii iii) is followed N-methyl-L-phenylalanine methyl ester hydrochloride in place of glycine methyl ester hydrochloride to give the title compound.

EXAMPLE 22

N-[{2-n-Butyl-1-(2-chlorophenyl)methyl-1H-imidazol-5-yl}methylcarbonyl]-(3 thienyl)alanine The title compound is prepared following the procedure of Example 12 (ii iii) using (3g thienyl)alanine methyl ester hydrochloride in place of glycine methyl ester hydrochloride.

EXAMPLE 23

N-[{2-n-Butyl-1-(2-chlorophenyl)-methyl-1H-imidazol-5-yl}methylcarbonyl](5 methyl-2 thienyl)alanine The title compound is prepared following the procedure of Example 12 (ii iii) using (5 methyl-2 -thienyl)alanine methyl ester hydrochloride in place of glycine methyl ester hydrochloride.

EXAMPLE 24

N-[{2-n-Butyl-1-(2-chlorophenyl)methyl-1H-imidazol-5-yl}methylcarbonyl]-(2 furyl)alanine The title compound is prepared following the procedure of Example 12 (ii–iii) using (2-furyl)alanine methyl ester hydrochloride in place of glycine methyl ester hydrochloride.

EXAMPLE 25

N-[{2-n-Butyl-1-(2-chlorophenyl)methyl-1H-imidazol-5-yl}methylcarbonyl]-(4-pyridyl)alanine The title compound is prepared following the procedure of Example 12 (ii–iii) using (4-pyridyl)alanine methyl ester hydrochloride in place of glycine methyl ester hydrochloride.

EXAMPLE 26

N-[[2-n-Butyl-1-(2-chlorophenyl)methyl-4-fluoro-1H-imidazol-5-yl]methylcarbonyl]phenylalanine The title compound is prepared following the procedure of Example 1-(iii–iv) using phenylalanine methyl ester hydrochloride in place of glycine methyl ester hydrochloride and using 2-[n-butyl-1-(2-chlorophenyl)-methyl-4-fluoro-1H-imidazol-5-yl]acetic acid (prepared as in U.S. Pat. No. 4,340,598) in place of 1-(2-chlorophenyl)methyl-2-propylthio-1H-imidazole-5 carboxylic acid.

EXAMPLE 27

N-[{2-n-Butyl-1-(2-chlorophenyl)-methyl-4-chloro-1H-imidazol-5-yl}methylcarbonyl]phenylalanine The title compound is prepared following the procedure of Example 1-(iii–iv) using phenylalanine methyl ester hydrochloride in place of glycine methyl ester hydrochloride and using 2-[n-butyl-1-(2-chlorophenyl)-methyl-4-chloro-1H-imidazol-5-yl]acetic acid (prepared as in U.S. Pat. No. 4,340,598) in place of 1-(2-chlorophenyl)methyl-2 propylthio-1H-imidazole-5-carboxylic acid.

EXAMPLE 28

N-[{2-n-Butyl-1-(2-chlorophenyl)methyl-4-phenyl-1H-imidazol-5-yl}methylcarbonyl]phenylalanine The title compound is prepared following the procedure of Example 1-(iii–iv) using phenylalanine methyl ester hydrochloride in place of glycine methyl ester hydrochloride and using 2-[n-butyl-1-(2-chlorophenyl)-methyl-4-phenyl-1H-imidazol-5-yl]acetic acid (prepared as in U.S. Pat. No. 4,340,598) in place of 1-(2-chlorophenyl)methyl-2-propylthio-1H-imidazole-5 carboxylic acid.

EXAMPLE 29

N-[{2-n Butyl-1-(2-methylphenyl)methyl-1H-imidazol-5-yl}methylcarbonyl]-L-(2 thienyl)alanine The title compound is prepared following the procedure of Example 12 (i–iii) using 2-methylbenzyl bromide in place of 2-chlorobenzyl bromide and L-(2-thienyl)alanine methyl ester hydrochloride in place lycine methyl ester hydrochloride.

EXAMPLE 30

N-[{2-n-Butyl 1-(2-methoxyphenyl)methyl-1H-imiazol-5-yl}methylcarbonyl]-L-(2-thienyl)alanine The title compound is prepared following the procedure of Example 12 (i–iii) using 2-methoxybenzyl bromide in place of 2-chlorobenzyl bromide and L-(2-thienyl)alanine methyl ester hydrochloride in place of glycine methyl ester hydrochloride.

EXAMPLE 31

N-[[2-n-Butyl-1-(3 methoxyphenyl)methyl-1H-imidazol-5-yl}methylcarbonyl]-L-(2-thienyl)alanine The title compound is prepared following the procedure of Example 12 (i—iii) using 3-methoxybenzyl bromide in place of 2-chlorobenzyl bromide and L-(2 thienyl)alanine methyl ester hydrochloride in place of glycine methyl ester hydrochloride.

EXAMPLE 32

N-[{2-n-Butyl-1-(4-phenylphenyl)methyl-1H-imidazol-5-yl)methylcarbonyl]-L-(2-thienyl)alanine The title compound is prepared following the procedure of Example 12 (i–iii) using 4-phenylbenzyl bromide in place of 2-chlorobenzyl bromide and L-(2-thienyl)alanine methyl ester hydrochloride in place of glycine methyl ester hydrochloride.

EXAMPLE 33

N-[{2-n-Butyl-1-(4-methoxy-3-methylphenyl)methyl-1H-imidazol-5-yl}methylcarbonyl]-L-(2-thienyl)alanine The title compound is prepared following the procedure of Example 12 (i–iii) using 4-methoxy-3-methylbenzyl bromide in place of 2-chlorobenzyl bromide and L-(2-thienyl)alanine methyl ester hydrochloride in place of glycine methyl ester hydrochloride.

EXAMPLE 34

N-[{2-n-Butyl-1-(2,3 dichlorophenyl)methyl-1H-imidazol-5-yl}methylcarbonyl]-L-(2 thienyl)alanine The title compound is prepared following the procedure of Example 12 (i iii) using 2,3-dichlorobenzyl bromide in place of 2-chlorobenzyl bromide and L (2-thienyl)alanine methyl ester hydrochloride in place of glycine methyl ester hydrochloride.

EXAMPLE 35

N-[2-n-Butyl-1-(2-nitrophenyl)methyl-1H 0imidazol-5-yl}methylcarbon-yl]-L (2-thienyl)alanine The title compound is prepared following the procedure of Example 12 (i–iii) using 2-nitrobenzyl bromide in place of 2-chlorobenzyl bromide and L-(2-thienyl)alanine methyl ester hydrochloride in place of glycine methyl ester hydrochloride.

EXAMPLE 36

N-[{2-n-Butyl-1-(2 trifluoromethylphenyl)methyl-1H-imidazol-5-yl}methylcarbonyl]-L (2-thienyl)alanine The title compound is prepared following the procedure of Example 12 (i–iii) using 2-trifluoromethylbenzyl bromide in place of 2-chlorobenzyl bromide and L-(2-thienyl)alanine methyl ester hydrochloride in place of glycine methyl ester hydrochloride.

EXAMPLE 37

N-[[2-(1-Adamantyl)ethyl]-2-n-butyl-1H-imidazol-5-yl}ethyl-2-carbonyl]-L-phenylalanine A mixture of 2-(1-adamantyl)ethanol and diisopropylethylamine in methylene chloride is added to triflic anhydride in methylene chloride at −78° C. under argon. After stirring the mixture at −78° C. for 45 minutes, 1-acetyl-2-n-butyl 5 (acetoxymethyl)imidazole in methylene chloride is added and the mixture is allowed to stand at room temperature for 4 days, then concentrated and heated on a steam bath with 10% sodium hydroxide, diluted with water, extracted with methylene chloride, dried, filtered and concentrated to give an oil. Chromatography (silica gel) in methanol chloroform gives 5-acetoxymethyl-1-[2-(1-adamantyl)ethyl]2-n-butylimidazole.

The above prepared compound is stirred at room temperature with potassium hydroxide in ethanol for one hour. The mixture is concentrated, poured into water, stirred and filtered to give 1-[2-(1-adamantyl)ethyl-2-n-butyl-5-hydroxymethylimidazole. The hydroxymethyl group is oxidized by refluxing the imidazole compound with manganese dioxide in toluene to give 1-[2 (1 adamantyl)ethyl]2-n-butyl imidazol-5-carboxaldehyde.

Diisopropylamine is covered with tetrahydrofuran and then 2.5 M n-butyl lithium in hexane is added. The mixture is stirred for 15 minutes, then trimethyl phosphonopropanoate in tetrahydrofuran is added. After 20 minutes, 1-[2-(1-adamantyl)ethyl]-2-n-butyl-imidazol-5-carboxaldehyde in tetrahydrofuran is added and the mixture is stirred for 30 minutes at −78° C. The mixture is poured into 40 ml of saturated ammonium chloride in water, extracted with ether, dried over magnesium sulfate, filtered, concentrated and chromatographed on silica gel eluting with ethyl acetate and hexane to give methyl 3-[1-(2 (1-adamantyl)ethyl)-2-n-butyl-1H-imidazol-5-yl]-3-hydroxypropanoate. To this compound in methylene chloride is added 4-dimethylaminopyridine, then acetic anhydride is added dropwise. The mixture is stirred for one hour, then poured into water and worked up to give 3-acetoxy-3-[1-(2-(1-adamantyl)ethyl-2-n-butyl-1H-imidazol-5-yl]propanoate.

The above prepared compound is heated with 1,8-diazabicyclo[5,4,0]undec-7-ene in toluene at 80° C. with stirring for one hour. The mixture is concentrated, then stirred with ether. The ether layer is decanted and dried, filtered, concentrated and chromatographed to give methyl-3-[1-(2-(1-adamantyl)ethyl)-2-n-butyl-1H-imidazol-5-yl]propenoate.

The title compound is prepared following the procedure of Example 11 (ii–iii) using methyl 3-[1-(2-(1-adamantyl)ethyl)-2-n-butyl 1H-imidazol-5-yl]propenoate in place of methyl-3-[2-n-butyl-1-{(2-chlorophenyl)methyl}-1H-imidazol-5-yl]propenoate.

Alternatively, the sodium salt of the acid is isolated directly from the reaction mixture, prior to neutralization. The crude basic reaction solution is applied to a reverse-phase flash column equilibrated with water. The inorganics are washed from the column with water (3 void volumes) and then the product is eluted with a 50:50 mixture of acetonitrile in water. The aceto nitrile is removed in vacuo and then the desired sodium salt is obtained after lyophilization.

EXAMPLE 38

N-[{1-(2-chlorophenyl)methyl-2-propenylthio-1H-imidazol-5-yl}carbonyl]-L-phenylalanine The title compound is prepared following the procedure of Example 1-(i–iv) using allyl bromide in place of propyl bromide and using L-phenylalanine methyl ester hydrochloride in place of glycine methyl ester hydrochloride.

EXAMPLE 39

N-[{1-(2-chlorophenyl)methyl-2-pentylthio-1H-imidazol-5-yl}carbonyl]-L-phenylalanine The title compound is prepared followinq the procedure of Example 1-(i–iv) using 1-bromopentane in place of propyl bromide and usinq L-phenylalanine methyl ester hydrochloride in place of glycine methyl ester hydrochloride.

EXAMPLE 40

N-[{1-(2-chlorophenyl)methyl-2-benzylthio-1H-imidazol-5-yl}carbonyl]-L-phenylalanine The title compound is prepared followinq the procedure of Example 1-(i–iv) usinq benzyl bromide in place of propyl bromide and using L-phenylalanine methyl ester hydrochloride in place of glycine methyl ester hydrochloride.

EXAMPLE 41

N-[1-(2-chlorophenyl)methyl-2-hexylthio-1H-imidazol-5-yl}carbonyl]-L-phenylalanine The title compound is prepared following the procedure of Example 1-(i–iv) using cyclohexyl bromide in place of propyl bromide and using L-phenylalanine methyl ester hydrochloride in place of glycine methyl ester hydrochloride.

EXAMPLE 42

N-1-(2-chlorophenyl)methyl-2-heptylthio-1H-imidazol-5-yl}carbonyl]-L-phenylalanine The title compound is prepared following the procedure of Example 1-(i–iv) using 1-bromoheptane in place of propyl bromide and using L-phenylalanine methyl ester hydrochloride in place of glycine methyl ester hydrochloride.

EXAMPLE 43

N-[{1-(2-chlorophenyl)methyl-2 hexenylthio-1H-imidazol-5-yl}carbonyl]-L-phenylalanine The title compound is prepared followinq the procedure of Example 1-(i–iv) using 6-bromo-1-hexene in place of propyl bromide and using L-phenylalanine methyl ester hydrochloride in place of glycine methyl ester hydrochloride.

EXAMPLE 44

N-[{1-(2-chlorophenyl)methyl-2 cyclopropylthio-1H-imidazol-5-yl}carbonyl]-L-phenylalanine The title compound is prepared following the procedure of Example 1-(i–iv) using cyclopropyl bromide in place of propyl bromide and using L-phenylalanine methyl ester hydrochloride in place of glycine methyl ester hydrochloride.

EXAMPLE 45

N-[{2-n-Butyl-1-(2-chlorophenyl)methyl-4-hydroxymethyl-1H-imidazol-5-yl}ethyl-2-carbonyl}L (2 thienyl)alanine (i) 2-n-butyl-1-(2-chlorophenyl)methyl-4-(t butyldimethylsilyloxy)methyl-1H-imidazol-5-carboxaldehyde A solution of 2-n-butyl-1-(2-chlorophenyl)methyl-4,5 bis(hydroxy)methyl-1H-imidazole (Example 11, (i)(b) (310 mg, 1 mmol) in methylene chloride (5 mL) was treated with 4-dimethylaminopyridine (5.2 mg), triethylamine (1.5 mmol) and t butyl dimethylsilyl chloride (192 mg, 1.24 mmol). The mixture was stirred at 25° C. for 20 hours, diluted with water and the organic layer was washed well with water, dried, concentrated and chromatographed over silica gel with an ethyl acetate/methanol gradient to afford 127 mg (24%) of the bis (4,5 t butyldimethylsilyl) ether and 252 mg (59%) of 2-n butyl-1-(2-chlorophenyl)methyl-4-t-butyldimethysilyloxymethyl-5-hydroxymethyl-1H-imidazole. This monoether (252 mg) was oxidized to the 5-carboxaldehyde using manganese dioxide to provide 170 mg of 2-n-butyl-1-(2-chlorophenyl)methyl-4-(t-butyldimethylsilyloxy)methyl-1H-imidazol-5-carboxaldehyde as an oil.

(ii) methyl (E)-3-[2-n-butyl-1-{(2-chlorophenyl)methyl}-4-(t-butyldimethylsilyloxy)methyl-1H-imidazol-5-yl]-2-propenoate To tetrahydrofuran (80 mL) is added n butyl lithium (15.5 mmol in hexane) and at −78° C. under argon is then added diisopropylamine (2.4 mL, 17.1 mmol). Methyl propanoate (15.3 mmol) is added neat over 5–6 minutes, and the mixture was stirred an additional 30 minutes at −78° C. A solution of 2-n-butyl-1-(2-chlorophenyl)methyl-4-(t-butyldimethylsilyloxy)methyl-1H-imidazol-5-carboxaldehyde (10.2 mmol) in tetrahydrofuran (10 mL) is added via a cannula, and the reaction mixture is stirred for 15 minutes. The reaction is partitioned between saturated ammonium chloride and ether, and the ether layer is washed with water, dried and concentrated to give crude product. This is chromatographed over silica gel with 20–50% of ethyl acetate in hexane to afford a mixture of isomeric β-hydroxyester products. A solution of this mixture (8.54 mmol) in methylene dichloride (100 mL) is treated with 4 dimethylaminopyridine (3 mmol) followed by acetic anhydride (84 mmol), and the solution is stirred at room temperature for 5 hours. The reaction is poured into water, stirred for 20 minutes and the product is extracted into ether. The ether extracts are washed with dilute hydrochloric acid solution, water, sodium bicarbonate solution and brine. The dried, concentrated mixture of β-acetoxyester products is used directly in the elimination reaction. To a solution of the β-acetoxyester product (4.5 mmol) in toluene (60 mL) is added of 1,8-diazabicyclo[5.4.0]undec-7-ene (DBU) (10.9 mmol), and the mixture is heated at 90° C. for 24 hours. The reaction is concentrated to 10 mL, diluted with ether and flash filtered through a 14×3 cm plug of silica gel with ether rinses to afford the crude olefinic product. Chromatography over silica gel with an ethyl acetate in hexane gradient gives homogeneous methyl (E) 3-[2-n- butyl-1-{(2-chlorophenyl)methyl}-4-(t-butyldimethylsilyloxy)methyl-1H-imidazol-5-yl]-2-propenoate. The elimination of the acetate with DBU produces predominantly the trans (E) isomer.

(iii)
methyl-3-[2-n-butyl-1-{(2-chlorophenylmethyl}-4-(t-butyldimethylsilyloxy)methyl-1H-imidazol-5-yl]propanoate The unsaturated ester is reduced to the corresponding saturated ester by catalytic hydrogenation. The vinyl compound is dissolved in ethanol, platinum oxide is added and then the suspension is stirred under an atmosphere of hydrogen for 1.5 hours to give methyl 3-[2-n-butyl-1-{(2-chlorophenyl)methyl}-4-(t-butyldimethylsilyloxy)methyl 1H-imidazol-5-yl]propanoate.

(iv)
3-[2-n-butyl-1-[(2-chlorophenyl)methyl]-4-(t-butyldimethylsilyloxy)methyl-1H-imidazol-5-yl]propanoic acid A solution of ethyl (E) 3-[2-n-butyl-1-{(2-chlorophenyl)methyl-4-(t-butyldimethylsilyoxy)methyl-1H-imidazol-5-yl]propanoate (0.287 mmol) in absolute ethanol (3 mL) is treated portionwise with one equivalent of 10% sodium hydroxide solution. After being stirred overnight at 25° C., the reaction is heated 50° C. for 4 hours, then concentrated in vacuo. The residual product is taken up in water, acidified to pH 5-6 and extracted with methylene chloride. The isolated, dried, concentrated product is triturated with methanol/ether to provide the title compound.

(v)
N-[{2-n-butyl-1-(2-chlorophenyl)methyl-4-(t-butyldimethylsilyloxy)methyl-1H-imidazol-5-yl}ethyl-2-carbonyl]-L-(2 thienyl)alanine methyl ester The above compound is prepared following the procedure of Example 1-(iii) using 3-[2-n-butyl-1-{(2-chlorophenyl)methyl}-4-(t-butyldimethylsilyloxy)-methyl-1H-imidazol-5-yl]propanoic acid in place of 1-(2-chlorophenyl)methyl-2 propylthio-1H-imidazole-5-carboxylic acid and using L-(2-thienyl)alanine hydrochloride in place of glycine methyl ester hydrochloride.

(vi)
N-[{2-n-butyl-1-(2-chlorophenyl)methyl-4-hydroxymethyl-1H-imidazol-5-yl}ethyl-2-carbonyl]-L-(2 thienyl)alanine The title compound is prepared following the procedure of Example 1-(iv) using N {2-n-butyl-1-(2-chlorophenyl)methyl-4-(t-butyldimethylsilyloxy)methyl-1H-imidazol-5-yl}ethyl-2-carbonyl]-L-(2-thienyl)alanine methyl ester in place of N-[{1-(2-chlorophenyl)methyl-2-propylthio-1H-imidazol-5-yl}carbonyl]glycine methyl ester.

EXAMPLE 46

N-[{2-n Butyl-1-(2-chlorophenyl)methyl-4-formyl-1H-imidazol-5-yl}ethyl-2-carbonyl}-L-(2-thienyl)alanine The title compound is prepared by dilute hydrochloric acid hydrolysis of the 4-t-butyldimethylsilyloxy group of N-[(2-n butyl-1-(2-chlorophenyl)methyl-4-(t-butyldimethyl-silyloxy)methyl-1H-imidazol-5-yl}ethyl-2-carbonyl]-L-(2-thienyl)alanine methyl ester, prepared in Example 45 (v), followed by manganese dioxide oxidation of the 4-hydroxy methyl group to the carboxaldehyde and hydrolysis of the ester group to the acid.

EXAMPLE 47

N-[{2-n-Butyl-1-(2-chlorophenyl)methyl-4-carboxy-1H-imidazol-5-yl}ethyl-2-carbonyl}-L-(2-thienyl)alanine N-[(2-n-butyl-1-(2-chlorophenyl)methyl-4-hydroxymethyl-1  1H-imidazol-5-yl}ethyl-2-carbonyl]-L-(2-thienyl)alanine, prepared in Example 45, is esterified with 4-methoxybenzyl alcohol to give the p-methoxybenzyl ester. The 4 hydroxymethyl group on the imidazole is oxidized using an acidic solution containing chromic acid (Jones' reagent) in acetone and the ester is hydrolyzed using 10% sodium hydroxide to give the title compound.

EXAMPLE 48

N-[{2-n-Butyl-1-(2-chlorophenyl)methyl-4-carbamoyl-1H-imidazol-5-yl}ethyl-2-carbonyl}-L-(2-thienyl)alanine The 4-methoxybenzyl ester, prepared in Example 47, is treated with oxalyl chloride in methylene chloride at 0° C. to give the 4-chloroformylimidazole derivative which is treated with ammonium hydroxide to give the 4-carbamoyl ester compound. The ester is hydrolyzed to give the title compound.

EXAMPLE 49

N-[{2-n-Butyl-1-(2-chlorophenyl)methyl-4-dimethylcarbamoyl-1H-imidazol-5-yl}ethyl2-carbonyl}-L-(2-thienyl)alanine Treating the 4 chloroformyl imidazole, prepared in Example 48, with dimethylamine instead of ammonium hydroxide gives the title compound.

EXAMPLE 50

(S)-2-Butyl-1-[(2-chlorophenyl)methyl-N-[1-1H-tetrazol-5-yl)-2-(2-thienyl)-ethyl[-1H-imidazole-5-acetamide The title compound is prepared following the procedure of Example (iii-iv) using 2-[2-n-butyl-1-(2-chlorophenyl)methyl-1H-imidazol-5-yl]acetic acid, prepared in Example 12 (i), in place of 1-(2-chlorophenyl)methyl-2-propylthio-1H-imidazole-5-carboxylic acid and using α-(1H-tetrazol-5-yl)-α-[(2-thienyl)methyl]methanamine [prepared by the procedure described in J. Pharm. Sciences, 66:1642-1644 (1977)] in place of glycine methyl ester hydrochloride.

EXAMPLE 51

(S)-2-Butyl-1-[(2-chlorophenyl)methyl-N-[2-phenyl-1-(1H-tetrazol-5-yl)ethyl]-1H-imidazole-5-acetamide The title compound is prepared following the procedure of Example (iii-iv) using 2-[2-n-butyl-1-( 2-chlorophenyl)methyl-1H-imidazol-5-yl]acetic acid, prepared in Example 12 (i), in place of 1-(2-chlorophenyl)methyl-2-propylthio 1H-imidazole-5-carboxylic acid and using α-(phenyl)methyl-α-(1H  -tetrazol-5-yl)-methanamine [prepared by the procedure described in J. Pharm. Sciences, 66:1642 1644 (1977)] in place of glycine methyl ester hydrochloride.

EXAMPLE 52

(S)-2-Butyl-1-[(2,3-dichlorophenyl)methyl-N-[1-(1H-tetrazol-5-yl)-2-(2-thienyl)ethyl]-1H-imidazole-5-acetamide The title compound is prepared following the procedure of Example 12 (i–iii) using 2,3-dichlorobenzyl bromide in place of 2-chlorobenzyl bromide and α-(1H-tetrazol-5-yl)-α-[(2-thienyl)methyl]methanamine in place of glycine methyl ester hydrochloride.

EXAMPLE 53

(S)-2-Butyl-1-[(2,3-dichlorophenyl)methyl-N-2-phenyl-1-(1H-tetrazol-5-yl)ethyl]-1H-imidazole-5-acetamide The title compound is prepared following the procedure of Example 12 (i–iii) using 2,3 dichlorobenzyl bromide in place of 2-chlorobenzyl bromide and α-(phenyl)methyl-α-(1H-tetrazol-5-yl)methanamine in place of glycine methyl ester hydrochloride.

EXAMPLE 54

(S)-2-Butyl-1-[(2-nitrophenyl)methyl-N-[1-(1H-tetrazol-5-yl)-2-(2-thienyl)ethyl]-H-imidazole-5-acetamide The title compound is prepared followinq the procedure of Example 12 (i–iii) using 2-nitrobenzyl bromide in place of 2-chlorobenzyl bromide and α-(1H-tetrazol-5-yl)-α-[(2-thienyl)methyl]methanamine in place of glycine methyl ester hydrochloride.

EXAMPLE 55

(S)-2-Butyl-1-[(2-nitrophenyl)methyl-N-[2-phenyl-1-(1H-tetrazol-5-yl)ethyl]-1H-imidazole-5-acetamide The title compound is prepared followinq the procedure of Example 12 (i–iii) usinq 2-nitrobenzyl bromide in place of 2-chlorobenzyl bromide and α-(phenyl)-methyl-α-(1H-tetrazol-5-yl)methanamine in place of glycine methyl ester hydrochloride.

EXAMPLE 56

An oral dosage form for administering orally active Formula (I) compounds is produced by screening, mixing and filling into hard gelatin capsules the ingredients in proportions, for example, as shown below.

| Ingredients | Amounts |
| --- | --- |
| N-[{2-n-butyl-1-(2-chlorophenyl)-methyl-1H-imidazol-5-yl}methyl-carbonyl]-L-(2-thienyl)alanine | 100 mg |
| magnesium stearate | 10 mg |
| lactose | 100 mg |

EXAMPLE 57

The sucrose, calcium sulfate dihydrate and orally active Formula (I) compounds are mixed and granulated with a 10% gelatin solution. The wet granules are screened, dried, mixed with the starch, talc and stearic acid, screened and compressed into a tablet.

| Ingredients | Amounts |
| --- | --- |
| N-[{2-n-butyl-1-(2-chlorophenyl)-methyl-1H-imidazol-5-yl}methyl-carbonyl]-L-phenylalanine | 75 mg |
| calcium sulfate dihydrate | 100 mg |
| sucrose | 15 mg |
| starch | 8 mg |
| talc | 4 mg |
| stearic acid | 2 mg |

EXAMPLE 58

N-[[1-(2 Chlorophenyl)methyl-2-propylthio-1H-imidazol-5-yl}carbonyl]-L-phenylalanine, 50 mg, is dispersed in 25 ml of normal saline to prepare an injectable preparation.

EXAMPLE 59

A topical opthamological solution for administering Formula (I) compounds is produced by mixing under sterile conditions the ingredients in proportions, for example, as shown below.

| Ingredients | Amounts (mg/mL) |
| --- | --- |
| N-[{2-n-butyl-1-(2-chlorophenyl)-methyl-1H-imidazol-5-yl}methyl-carbonyl]-L-phenylalanine | 1.0 mg |
| dibasic sodium phosphate | 10.4 mg |
| monobasic sodium phosphate | 2.4 mg |
| chlorobutanol | 5.0 mg |
| hydroxypropanol methylcellulose | 5.0 mg |
| sterile water | 9.5 ad 1.0 mL |
| 1.0N sodium hydroxide | 9.5 ad pH 7.4 |

It is to be understood that the invention is not limited to the embodiments illustrated hereabove and the right to the illustrated embodiments and all modifications coming within the scope of the followinq claims is reserved.

What is claimed is:

1. A compound of the formula:

$$R^1-X-\underset{N}{\underset{\|}{\overset{N}{\overset{\|}{\bigcirc}}}}\underset{R^2}{\overset{(CH_2)_mR}{\underset{}{}}}(CH_2)_n-\underset{\|}{\overset{R^3}{C}}-N-\underset{R^4}{\overset{R^3}{C}}-R^5$$

in which:

R is adamantyl, or naphthyl, biphenyl, or phenyl, with each aryl group being unsubstituted or substituted by one to three substituents selected from halo, $C_{1-6}$alkyl, $C_{1-6}$alkoxy, OH, CN, $CO_2R^3$, tetrazol-5-yl, $SO_3H$, $SO_2NHR^3$, $NO_2$, W, $SC_{1-6}$alkyl, $SO_2C_{1-6}$alkyl, $NHSO_2R^3$, $PO(OR^3)_2$, $CONR^3R^3$, $NR^3R^3$, $NR^3COH$, $NR^3COC_{1-6}$alkyl, $NR^3CON(R^3)_2$, $NR^3COW$, or $SO_2W$;

$R^1$ is $C_{2-10}$alkyl, $C_{3-10}$alkenyl, $(CH_2)_{0-8}C_{3-6}$cycloalkyl, or $(CH_2)_{0-8}$phenyl unsubstituted or substituted by one to three substituents selected from $C_{1-6}$alkyl, $C_{1-6}$alkoxy, halo, OH, $NO_2$, $NR^3R^3$, W, $CO_2R^3$, CN, , $CONR^3R^3$, $NR^3COH$, tetrazol-5-yl, $NR^3COC_{1-6}$alkyl, $NR^3COW$, $SC_{1-6}$alkyl, $SO_2W$, or $SO_2C_{1-6}$alkyl;

X is a single bond, S, $NR_3$, or O;

m is 0–4;

$R^2$ H, $C_{1-6}$alkyl, halo, W, CHO, $CH_2OH$, $CO_2R^3$, $CONR^3R^3$, $NO_2$, CN, $NR^3R^3$, or phenyl;

each $R^3$ independently is H or $C_{1-6}$alkyl;

$R^4$ is H, $C_{1-8}$alkyl, thienyl-Y-, furyl-Y-, pyrazolyl-Y-, imidazolyl-Y-, thiazolyl-Y-, pyridyl-Y-, tetrazolyl-Y-, pyrrolyl-Y-, triazolyl-Y-, oxazolyl-Y-, isoxazolyl-Y-, or phenyl-Y-, with each aryl or heteroaryl group being unsubstituted or substituted by $C_{1-6}$alkyl, $C_{1-6}$alkoxy, halo, $NR^3R^3$, $CO_2R^3$, OH, $NO_2$, $SO_2NHR^3$, $SO_3H$, $CONR^3R^3$, W, $SO_2W$, $SC_{1-6}$alkyl, $SO_2C_{1-6}$alkyl, $NR^3COH$, $NR^3COW$, or $NR^3COC_{1-6}$alkyl;

$R^5$ is $CO_2R^3$, $CONR^3R^3$, or tetrazol-5-yl;

W is $C_qF_{2q+1}$, wherein q is 1-4;

Y is a single bond or $C_{1-6}$alkyl which is straight or branched; and n is 0-5; or a pharmaceutically acceptable salt thereof.

2. A compound of claim 1 in which:

R is phenyl unsubstituted or substituted by one to three substituents selected from chloro, fluoro, nitro, carboxy, trifluoromethyl, methyl, methoxy, hydroxy, sulfonamido, sulfamyl, cyano, carbo$C_{1-6}$alkoxy, carbamoyl, or tetrazol-5-yl;

$R^1$ is $C_{2-8}$alkyl;

X is a single bond or S;

m is 0, 1 or 2;

$R^2$ is hydrogen, chloro, fluoro, or trifluoromethyl;

each $R^3$ is independently hydrogen or methyl;

$R^4$ is hydrogen, $C_{1-4}$alkyl, phenyl $(CH_2)_{0-2}$, or thienyl-$CH_2$;

$R^5$ is $CO_2R^3$ or tetrazol-5-yl; and n is 0-3; or a pharmaceutically acceptable salt thereof;

3. A compound of claim 2 which is N-]{2-n-butyl-1(2-chlorophenyl)methyl-1H-imidazol-5-yl}methylcarbonyl]-L-(2-thienyl)alanine or a pharmaceutically acceptable salt thereof.

4. A compound of claim 2 which is N-[{2-n-butyl-1-(2-chlorophenyl)methyl-1H-imidazol-5-yl}methylcarbonyl]-L-phenylalanine or a pharmaceutically acceptable salt thereof.

5. A compound of claim 2 which is N-[{1-(2-chlorophenyl)methyl-2-propylthio-1H-imidazol-5-yl}methylcarbonyl]-L-phenylalanine or a pharmaceutically acceptable salt thereof 6. A compound of claim 2 which is:

N-[{2-n butyl-1-(2-chlorophenyl)methyl-1H-imidazol-5-yl}methylcarbonyl]glycine;

N-[[1-(2-chlorophenyl)methyl-2-propylthio-1H-imidazol-5-yl}methylcarbonyl]-L-homophenylalanine;

N-[(2-n-butyl-1-chlorophenyl)methyl-1H-imidazol-5-yl}ethyl-2-carbonyl]-L-phenylalanine;

N-[{2-n-butyl-1-(2-chlorophenyl)methvl- 1H-imidazol-5-yl}methylcarbonyl]-L-isoleucine;

N-[[1-(2-chlorophen-yl)methyl-2-propylthio-1H-imidazol-5-yl}carbonyl]-D-phenylalanine; or N-[[1-(2-chlorophenyl)methyl-2-propylthio-1H-imidazol-5-yl}carbonyl]glycine;

or a pharmaceutically acceptable salt thereof.

7. A pharmaceutical composition comprising a compound of claim 1 and a suitable pharmaceutical carrier.

8. A pharmaceutical composition of claim 7 wherein the compound is N-[{2-n-butyl-1-(2-chlorophenyl)-methyl-1H-imidazol-5-yl}methylcarbonyl]-L-(2-thienyl)alanine.

9. A pharmaceutical composition of claim 7 wherein the compound is N-[{2-n-butyl-1-(2-chlorophenyl)-methyl-1H-imidazol-5-yl}methylcarbonyl]-L-phenylalanine.

10. A pharmaceutical composition of claim 7 wherein the compound is N-[{1-(2-chlorophenyl)methyl-2propylthio-1H-imidazol-5-yl}methylcarbonyl]-L-phenylalanine.

11. A pharmaceutical composition of claim 7, wherein the compound is:

N-[{2-n-butyl-1-(2-chlorophenyl)methyl-1H-imidazol-5-yl}methylcarbonyl]glycine;

N-[{1-(2-chlorophenyl)methyl-2-propylthio-1H-imidazol-5-yl}methylcarbonyl]-L-homophenylalanine;

N-[{2-n-butyl-1-chlorophenyl)methyl-1H-imidazol-yl}ethyl-2-carbonyl]-L-phenylalanine;

N-[{2-n-butyl-1-(2-chlorophenyl)methyl-1H-imidazol-5-yl}methylcarbonyl]-L-isoleucine;

N-[1-(2-chlorophenyl)methyl-2-propylthio-1H-imidazol-5-yl}carbonyl]-D-phenylalanine; or N-[{1-(2-chlorophenyl)methyl-2-propylthio-1H imidazol-5-yl}carbonyl]glycine.

12. A method of antagonizing angiotensin II receptors in mammals which comprises administering to a subject in need thereof an effective amount of a compound of claim 1.

13. A method of claim 12 wherein the compound is L-N-[[2-n-butyl-1-(2-chlorophenyl)methyl-1H-imidazol-5-yl)methylcarbonyl]-L (2-thienyl)alanine.

14. A method of claim 12 wherein the compound is N-[(2-n-butyl-1-(2-chlorophenyl)methyl-1H-imidazol-5-methylcarbonyl]-L-phenylalanine.

15. A method of claim 12 wherein the compound is N-[{1-(2-chlorophenyl)methyl-2-propylthio-1H-imidazol-yl}methylcarbonyl]-L-phenylalanine.

16. A method of claim 12 wherein the compound is:

N-[(2-n-butyl-1-(2-chlorophenyl)methyl-1H-imidazol-5-yl}methylcarbonyl]glycine;

N-[{1-(2-chlorophenyl)methyl-2-propylthio-1H-imidazol-5-yl}methylcarbonyl]-L-homophenylalanine;

N-[{2-n-butyl-1-chlorophenyl)methyl-1H-imidazol-5-yl}ethyl-2-carbonyl]-L-phenylalanine;

N-[{2-n-butyl-1-(2-chlorophenyl)methyl-1H-imidazol-5-yl}methylcarbonyl]-L-isoleucine;

N-[{1-(2-chlorophenyl)methyl-2-propylthio-1H-imidazol-5-yl}carbonyl]-D-phenylalanine; or N-[{1-(2-chlorophenyl)methyl-2 propylthio-1H-imidazol-5-yl}carbonyl]glycine.

17. A method of treating hypertension in mammals which comprises administering to a subject in need thereof an effective amount of a compound of claim 1.

18. A method of treating congestive heart failure in mammals which comprises administering to a subject in need thereof an effective amount of a compound of claim 1.

19. A method of treating renal failure in mammals which comprises administering to a subject in need thereof an effective amount of a compound of claim 1.

20. A method of treating glaucoma in mammals which comprises administerinq to a subject in need thereof an effective amount of a compound of claim 1.

* * * * *